United States Patent
Meng et al.

(10) Patent No.: US 10,759,997 B2
(45) Date of Patent: Sep. 1, 2020

(54) POLYMERIZABLE COMPOUND, LIQUID CRYSTAL MEDIUM CONTAINING SAME AND LIQUID CRYSTAL DISPLAY DEVICE

(71) Applicant: SHIJIAZHUANG CHENGZHI YONGHUA DISPLAY MATERIAL CO., LTD., Shijiazhuang, Hebei (CN)

(72) Inventors: Jinsong Meng, Shijiazhuang (CN); Zhiliang Shi, Shijiazhuang (CN); Lei Zhao, Shijiazhuang (CN); Ming Li, Shijiazhuang (CN); Wei Zhang, Shijiazhuang (CN); Xing Zhang, Shijiazhuang (CN); Guoliang Yun, Shijiazhuang (CN)

(73) Assignee: SHIJIAZHUANG CHENGZHI YONGHUA DISPLAY MATERIAL CO., LTD., Shijiazhuang, Hebei (CN)

( * ) Notice: Subject to any disclaimer, the term of this patent is extended or adjusted under 35 U.S.C. 154(b) by 115 days.

(21) Appl. No.: 15/972,582

(22) Filed: May 7, 2018

(65) Prior Publication Data
US 2018/0320071 A1    Nov. 8, 2018

(30) Foreign Application Priority Data
May 5, 2017 (CN) .......................... 2017 1 0312825

(51) Int. Cl.
| | |
|---|---|
| *G02F 1/1333* | (2006.01) |
| *C09K 19/54* | (2006.01) |
| *C07C 69/602* | (2006.01) |
| *C07C 69/54* | (2006.01) |
| *C09K 19/12* | (2006.01) |
| *C09K 19/58* | (2006.01) |
| *C07C 69/653* | (2006.01) |
| *C09K 19/04* | (2006.01) |
| *C09K 19/30* | (2006.01) |

(52) U.S. Cl.
CPC ............ *C09K 19/542* (2013.01); *C07C 69/54* (2013.01); *C07C 69/602* (2013.01); *C07C 69/653* (2013.01); *C09K 19/12* (2013.01); *C09K 19/586* (2013.01); *C09K 19/588* (2013.01); *C09K 2019/0448* (2013.01); *C09K 2019/122* (2013.01); *C09K 2019/123* (2013.01); *C09K 2019/3016* (2013.01); *C09K 2019/3021* (2013.01); *C09K 2019/3025* (2013.01); *C09K 2019/3027* (2013.01); *C09K 2019/548* (2013.01)

(58) Field of Classification Search
CPC .... C09K 19/542; C09K 19/12; C09K 19/586; C09K 19/588; C09K 2019/0488; C09K 2019/122; C09K 2019/123; C09K 2019/3016; C09K 2019/3021; C09K 2019/3025; C09K 2019/3027; C09K 2019/548; G02F 1/1333; C07C 69/54; C07C 69/602; C07C 69/653
USPC ...................................................... 252/299.4
See application file for complete search history.

(56) References Cited

U.S. PATENT DOCUMENTS

2018/0320071 A1* 11/2018 Meng ................ C09K 19/12

* cited by examiner

*Primary Examiner* — Geraldina Visconti
(74) *Attorney, Agent, or Firm* — Paratus Law Group, PLLC

(57) ABSTRACT

Disclosed is a polymerizable compound having a structural formula as represented by the following formula I:

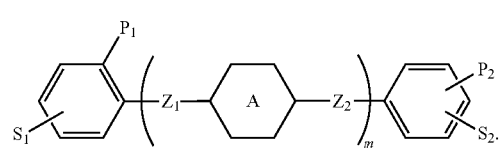

The polymerizable compound disclosed in the present invention has a plurality of ring systems, and the entire molecular structure thereof is curved and twisted. The present invention further discloses a liquid crystal medium comprising the polymerizable compound, the polymerizable compound provided by the present invention has an appropriate polymerization rate in the liquid crystal medium, and the liquid crystal medium can be well applied to a PS-(polymer stabilized)- or PSA-(polymer stabilized alignment)-type liquid crystal display device. Further disclosed is a liquid crystal display device prepared from the liquid crystal medium.

13 Claims, 2 Drawing Sheets

POLYMERIZABLE COMPOUND, LIQUID CRYSTAL MEDIUM CONTAINING SAME AND LIQUID CRYSTAL DISPLAY DEVICE

CROSS REFERENCE TO PRIOR APPLICATION

This application claims priority to Chinese Patent Application No. 201710312825.0 (filed on May 5, 2017), which is hereby incorporated by reference in its entirety.

TECHNICAL FIELD

The present invention relates to the technical field of liquid crystal materials. More specifically, the present invention relates to a polymerizable compound, a liquid crystal medium containing same and a liquid crystal display device.

BACKGROUND ART

Thin film transistor liquid crystal displays (TFT-LCDs) have undergone a long period of basic research, and after realising large-scale production and commercialisation, thin film transistor liquid crystal displays have become mainstream products in LCD applications due to the advantages of light weight, being environmentally friendly, high performance, etc., thereof: the application of TFT-LCD can be seen everywhere whether in small-sized mobile phone screens, large-sized notebook PCs or monitors or in large-sized liquid crystal televisions (LCD-TV).

Early commercial TFT-LCD products basically relate to using a TN display mode, and the largest problem thereof is a narrow viewing angle. With the increase in product size, especially the application in the TV field, an IPS display mode and a VA display mode, which have the characteristic of a wide viewing angle, have been sequentially developed and applied; in particular, based on the improvement of the VA display mode, the breakthrough development thereof has been achieved successively in major companies, which mainly depends on the advantages of a wide viewing angle, a high contrast, no need for frictional alignment, etc., of the VA mode itself. Furthermore, the contrast of the VA mode display is less dependent on the optical anisotropy (Δn) of the liquid crystal, the thickness of the liquid crystal cell (d) and the wavelength (λ) of the incident light, which will necessarily make the VA mode become a very promising display technique.

However, the liquid crystal medium used in an active matrix addressing mode display element for the VA mode, etc., itself is not perfect. The defects, for example, the residual image level is significantly worse than that of a positive dielectric anisotropic display element, the response time is relatively slow, and the driving voltage is higher. At this point, some new types of VA display techniques have quietly emerged: for example, a PSVA technique realises a wide viewing angle display mode similar to that of MVA/PVA, and also simplifies a CF process, such that the aperture ratio is increased while lowering the CF cost; furthermore, a higher brightness is obtained, thereby obtaining a higher contrast. In addition, since the liquid crystal of the entire panel has a pretilt angle, there is no domino delay phenomenon, a faster response time can also be obtained while maintaining the same drive voltage, and the residual image level will also not be affected; however, due to Fine Slit densely distributed electrodes in pixels, if the electrode width cannot be evenly distributed, the problem of uneven display can easily occur. Like a UVVA technique, on the basis of keeping the advantages of the PSVA technique, since there is no Slit structure on the TFT side, the problem of display unevenness caused by uneven pixel electrode width is also improved. Although the display device is continuously developing, people are still always devoted to studying new liquid crystal media, such that liquid crystal media and the performances of display devices in which the liquid crystal media are used can continuously advance forward.

Polymerizable mesogenic units (RMs) are currently a very popular and important topic in the display industry, and possible application fields thereof include polymer stabilized alignment (PSA) liquid crystal display, polymer stabilized blue-phase (PS-BP) liquid crystal display, pattern retarder films, etc.

The PSA principle is being applied to different typical LC displays such as PSA-VA, PSA-OCB, PS-IPS/FFS and PS-TN liquid crystal displays. Taking the most widely used PSA-VA display as an example, the pretilt angle of the liquid crystal cell can be obtained by a PSA method, and the pretilt angle has a positive effect on the response time. For PSA-VA displays, standard MVA or PVA pixel and electrode designs can be used; however, if a specially patterned design is used the electrode design on one side and no protrusion design is used on the other end, the production can be significantly simplified while the display is imparted with a very good contrast and a very high light transmittance.

It has been found in the prior art that LC mixtures and RMs still have some disadvantages in applications in PSA displays. First, so far not every desired soluble RM (polymerizable mesogen or polymerizable compound) is suitable for use in PSA displays; in addition, if it is desired to carry out a polymerization by means of a UV light without the addition of a photoinitiator (which may be advantageous for some applications), the choice becomes narrower; furthermore, a "material system" formed from an LC mixture (hereinafter also referred to as an "LC host mixture") in combination with the selected polymerizable component should have the lowest rotational viscosity and the best photovoltaic performance for increasing the "voltage holding ratio" (VHR) to achieve effects. In terms of PSA-VA, a high VHR after irradiation using a (UV) light is very important; otherwise, the problems of the occurrence of residual images to the display, etc., may be finally caused. So far, not all combinations of LC mixtures and polymerizable components are suitable for PSA displays. This is mainly due to the effects in the aspects of the UV-sensitive wavelength of polymerizable units being too short, or no tilt angle or an insufficient tilt angle occurring after light irradiation, or the polymerizable component having a poorer homogeneity after light irradiation, or the VHR after UV is lower for TFT display applications.

PS(A)-displays disclosed in the prior art generally comprise RM, wherein a ring system of the mesogenic group is bonded in para-position to the adjacent group (other ring, a bridging group, a spacer or a polymerizable group) thereto; for example, a display proposed in the publication of the invention patent with publication number EP 1498468 A1 comprises RM selected from the following formulas:

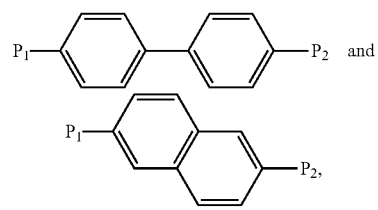

wherein P1 and P2 represent a polymerizable group such as an acrylate group, a methacrylate group, vinyl, vinyloxy or an epoxy group. However, the RMs as described in the above formulas generally have the problems of a high melting point and a limited solubility in many currently used liquid crystal mixtures, thus leading to ease of often spontaneously crystallising from the mixture.

In the publication of the invention patent with the publication number CN 101848978 A, a structure of formula Ra-(A1-Z1)m1-(A2-Z2)m2-(A3)m3-Rb I is proposed. The main improvement point thereof is that A1 and A3 each independently represent 1,3-phenylene, naphthalene-1,3-diyl, naphthalene-1,6-diyl, naphthalene-2,5-diyl or naphthalene-2,7-diyl, and compared to the RMs in the prior art, it shows a lower melting point, a lower crystallisation tendency and an improved solubility in many commercially available liquid crystal host mixtures.

However, it was found in the study that the RM monomer further has an important property, that is, the ratio of polymerization conversion, i.e., the rate of polymerization, within the same time under the irradiation of the same light intensity of UV light according to the panel process without adding any photoinitiator has an important effect on the panel yield. If the rate of polymerization is slow, the RM conversion will be incomplete and the effect of PSA (polymer stabilized alignment) will not be achieved; moreover, the liquid crystal medium is susceptible to deterioration when exposed to the UV light for a long time. If the rate of polymerization is too fast, polymerization particles will be too large, causing zara particles, which seriously affects the panel yield.

Thus, there has always been a great demand for PS(A)-displays, especially of VA and OCB types, and for liquid crystal media and RMs for use in these displays. In addition, these displays do not show the above-mentioned defects or only show the above-mentioned defects to a small extent and have improved properties. In particular, there is a great need for PS(A)-displays and liquid crystal media and RMs for use in such displays. As well-known and acknowledged, they need to have a high stability to prevent demixing at low temperatures, a high resistivity, a wide operating temperature range, a short response time (even at low temperatures), a low threshold voltage (which makes a large amount of grey scale, a high contrast, and a wide viewing angle possible), and a high "voltage holding ratio" (HR) value after UV exposure. In addition to the above-mentioned well known and acknowledged requirements, an RM monomer and a liquid crystal medium containing the RM monomer are also required to have an appropriate rate of polymerization to avoid the occurrence of panel failure.

The rate of polymerization of the RM monomer is closely related to the UV absorption spectrum thereof, and the main influence factors therefor are the main structure thereof, substituent groups, etc., wherein changes and effects brought about by different substituent groups are unpredictable. Slight changes in the RM structure may have a significant effect on the performance thereof.

SUMMARY OF THE INVENTION

In view of the above problems, it is a first objective of the present invention to provide a polymerizable compound.

It is a second objective of the present invention to provide a liquid crystal medium.

It is a third objective of the present invention to provide a liquid crystal display device.

In order to achieve the first objective, the present invention provides a polymerizable compound, characterized in that the structural formula of said polymerizable compound is as represented by the following formula I:

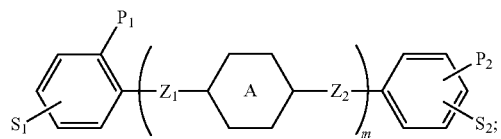

wherein $P_1$ and $P_2$ represent a substituent containing a polymerizable group;

$S_1$ and $S_2$ each independently represent H, a $C_1$-$C_5$ alkyl group, a $C_1$-$C_5$ alkoxy group, a fluorine-substituted $C_1$-$C_5$ alkyl group, a fluorine-substituted $C_1$-$C_5$ alkoxy group, a halogen, an acrylate group, or a methacrylate group, wherein any non-adjacent methylenes may be each independently replaced by —O—, —S—, —CH$_2$O—, —COO—, —OCH$_2$—, —OOC—, an acrylate group or a methacrylate group;

$Z_1$ and $Z_2$ each independently represent a single bond, —CH$_2$—, —CH$_2$CH$_2$—, —O—, —CH$_2$O—, —OCH$_2$—, —COO—, —OOC—, or an acrylate group;

represents 1,4-phenylene, or a 1,4-phenylene mono- or poly-substituted with one or more of H, a $C_1$-$C_5$ alkyl group, a $C_1$-$C_5$ alkoxy group, a fluorine-substituted $C_1$-$C_5$ alkyl group, a fluorine-substituted $C_1$-$C_5$ alkoxy group, a halogen, an acrylate group and a methacrylate group, wherein any non-adjacent methylenes of the $C_1$-$C_5$ alkyl group, $C_1$-$C_5$ alkoxy group, fluorine-substituted $C_1$-$C_5$ alkyl group, and fluorine-substituted $C_1$-$C_5$ alkoxy group may be each independently replaced by —O—, —S—, —CH$_2$O—, —COO—, —OCH$_2$—, —OOC—, an acrylate group or a methacrylate group;

m represents 0, 1 or 2;

when m represents 0, neither $S_1$ nor $S_2$ is H, or only $S_2$ is not H and $P_2$ is not in the ortho-position of the single bond linking the two benzene rings; and when m represents 1 or 2, $Z_1$ and $Z_2$ are not simultaneously a single bond, or

represents a 1,4-phenylene mono- or poly-substituted with one or more of a $C_1$-$C_5$ alkyl group, a $C_1$-$C_5$ alkoxy group, a fluorine-substituted $C_1$-$C_5$ alkyl group, a fluorine-substituted $C_1$-$C_5$ alkoxy group, a halogen, an acrylate group and a methacrylate group, wherein any non-adjacent methylenes of the $C_1$-$C_5$ alkyl group, $C_1$-$C_5$ alkoxy group, fluorine-substituted $C_1$-$C_5$ alkyl group, and fluorine-substituted $C_1$-$C_5$ alkoxy group may be each independently replaced by —O—, —S—, —CH$_2$O—, —COO—, —OCH$_2$—, —OOC—, an acrylate group or a methacrylate group.

Preferably, the structural formula of said polymerizable compound of structural formula I is specifically as represented by the following formula I-a:

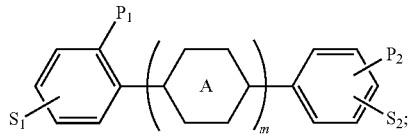

I-a wherein

P$_1$ and P$_2$ each independently represent an acrylate group, a methacrylate group, a fluorine-substituted acrylate group or a fluorine-substituted methacrylate group;

S$_1$ and S$_2$ each independently represent H, F, a C$_1$-C$_5$ alkyl group, a C$_1$-C$_5$ alkoxy group, a fluorine-substituted C$_1$-C$_5$ alkyl group, a fluorine-substituted C$_1$-C$_5$ alkoxy group, an acrylate group, a methacrylate group;

represents

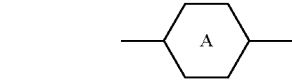

,

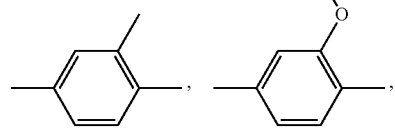

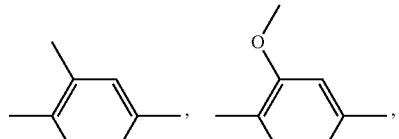

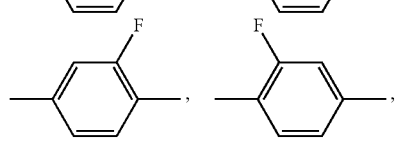

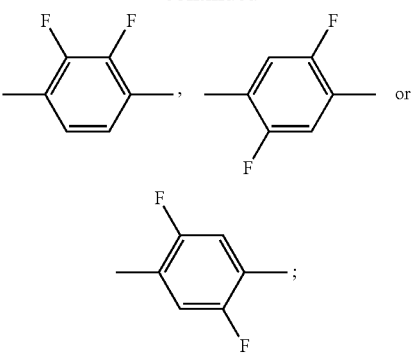

-continued m represents 0 or 1; and when m represents 0, neither S$_1$ nor S$_2$ is H, or only S$_2$ is not H and P$_2$ is not in the ortho-position of the single bond linking the two benzene rings; and when m represents 1,

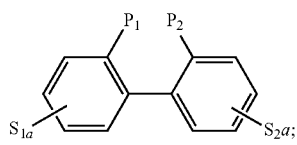

is not

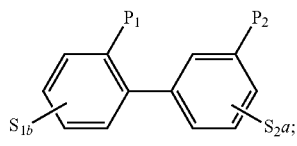

.

Further preferably, the structural formula of said polymerizable compound of structural formula I is specifically at least one of formulas I-1 to I-6 below:

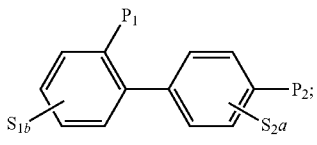

I-1

I-2

I-3

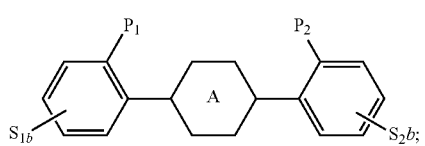

I-4

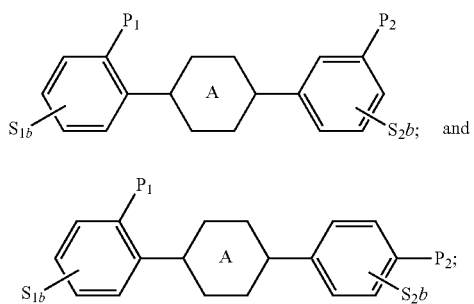

I-5

I-6 wherein

P$_1$ and P$_2$ each independently represent an acrylate group or a methacrylate group;

S$_{1a}$ represents F, methyl or methoxy;

S$_{1b}$ represents H, F, methyl or methoxy;

S$_2$a represents F, methyl or methoxy;

S$_2$b represents H, F, methyl or methoxy;

 represents

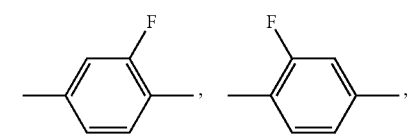

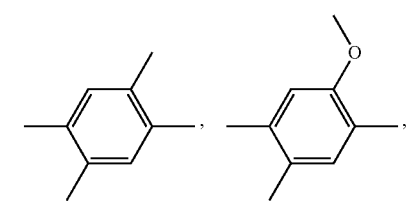

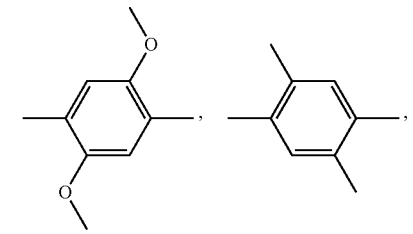

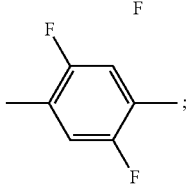

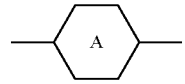

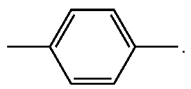

and when S$_2$b represents H,

is not

.

In order to achieve the second objective as described above, the present invention further provides a liquid crystal medium comprising one or more of the above-mentioned polymerizable compounds.

Preferably, said liquid crystal medium further comprises one or more compounds of structural formulas II-1 to II-12 and/or of formula III:

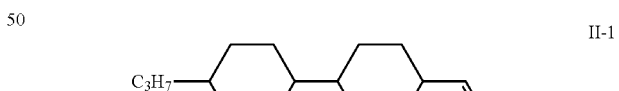 II-1

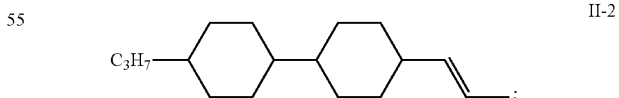 II-2

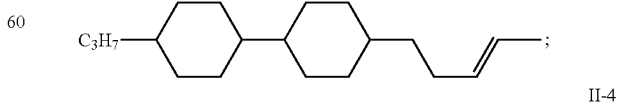 II-3

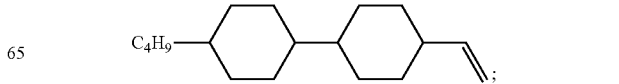 II-4

-continued

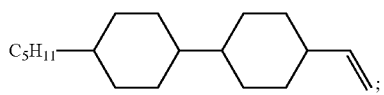
II-5

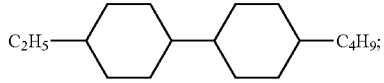
II-6

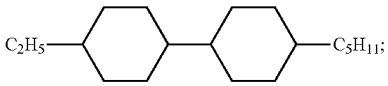
II-7

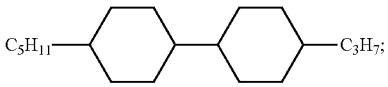
II-8

II-9

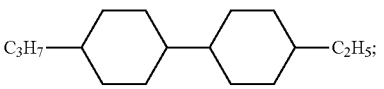
II-10

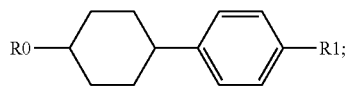
II-11

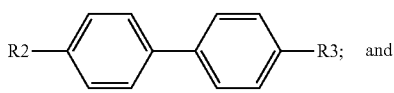
II-12  and

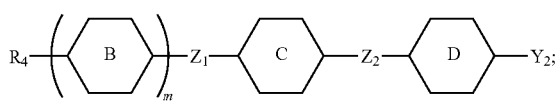
III wherein $R_0$, $R_1$, $R_2$ and $R_3$ each independently represent a $C_1$-$C_{10}$ alkyl group, a $C_2$-$C_{10}$ alkenyl group, or a $C_1$-$C_{10}$ alkoxy group, wherein any —$CH_2$— can be replaced by —O—, and any hydrogen can be replaced by F;

$R_4$ and $Y_2$ each independently represent H, F, a $C_1$-$C_{10}$ alkyl group, a fluorine-substituted $C_1$-$C_{10}$ alkyl group, a $C_1$-$C_{10}$ alkoxy group, a fluorine-substituted $C_1$-$C_{10}$ alkoxy group, a $C_2$-$C_{10}$ alkenyl group, a fluorine-substituted alkenyl group, a $C_3$-$C_8$ alkenyloxy group or a fluorine-substituted $C_3$-$C_8$ alkenyloxy group, wherein any one or more —$CH_2$— in $R_4$ may be replaced by cyclopentyl, cyclobutyl or cyclopropyl;

$Z_1$ and $Z_2$ each independently represent a single bond, —$CF_2O$—, —$CH_2CH_2$— or —$CH_2O$—;

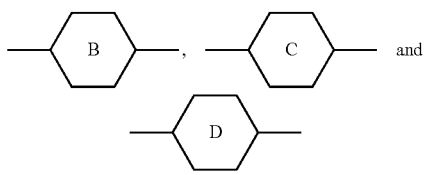

each independently represent

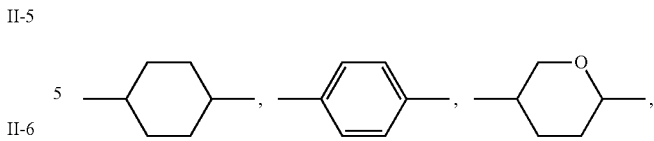

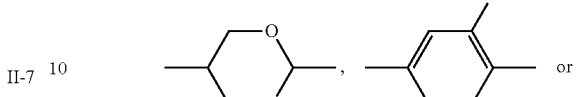

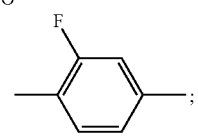

m represents 1 or 2.

Preferably, said liquid crystal medium further comprises one or more compounds of structural formula IV

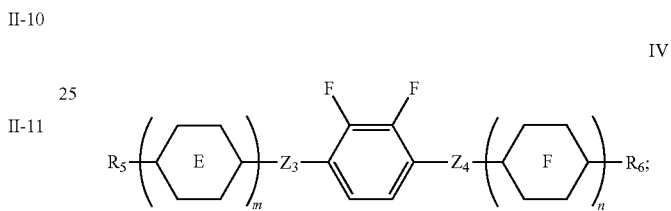
IV wherein $R_5$ and $R_6$ each independently represent H, F, a $C_1$-$C_{10}$ alkyl group; a fluorine-substituted $C_1$-$C_{10}$ alkyl group, a $C_1$-$C_{10}$ alkoxy group; a fluorine-substituted $C_1$-$C_{10}$ alkoxy group, a $C_2$-$C_{10}$ alkenyl group, a fluorine-substituted $C_2$-$C_{10}$ alkenyl group, a $C_3$-$C_8$ alkenyloxy group or a fluorine-substituted $C_3$-$C_8$ alkenyloxy group, wherein any one of —$CH_2$— in $R_5$ and $R_6$ may be replaced by cyclopentyl, cyclobutyl or cyclopropyl;

$Z_3$ and $Z_4$ each independently represent a single bond, —$CH_2CH_2$— or —$CH_2O$—;

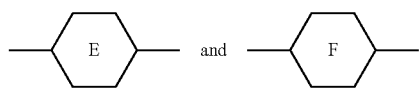

each independently represent one of

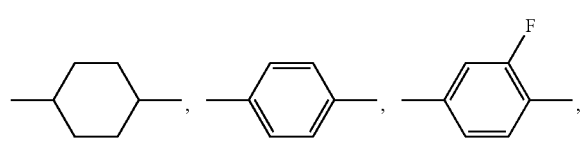

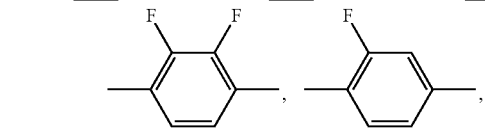

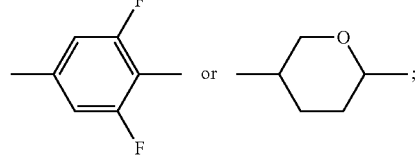

m represents 1 or 2; and n represents 0, 1 or 2.

Preferably, the structural formula of said compound of structural formula III is specifically at least one of formulas III-1 to III-9 below:

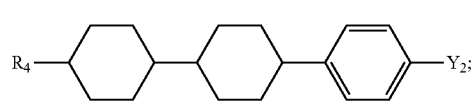
III-1

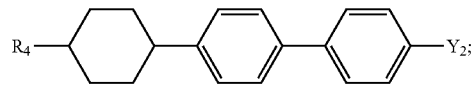
III-2

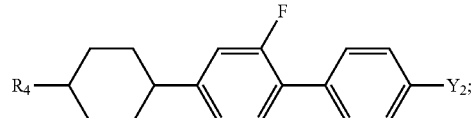
III-3

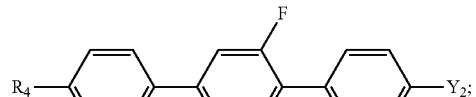
III-4

III-5

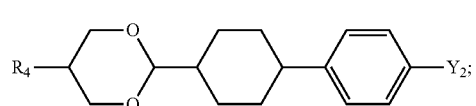
III-6

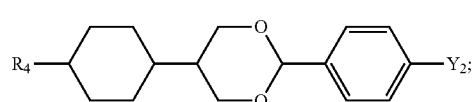
III-7

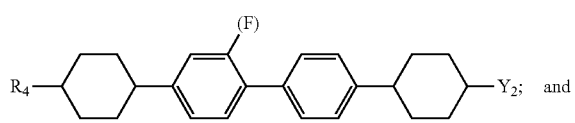
III-8

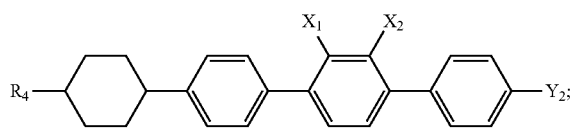
III-9 wherein $R_4$ and $Y_2$ each independently represent H, F, a $C_1$-$C_{10}$ alkyl group, a fluorine-substituted $C_1$-$C_{10}$ alkyl group, a $C_1$-$C_{10}$ alkoxy group, a fluorine-substituted $C_1$-$C_{10}$ alkoxy group, a $C_2$-$C_{10}$ alkenyl group, a fluorine-substituted $C_2$-$C_{10}$ alkenyl group, a $C_3$-$C_8$ alkenyloxy group or a fluorine-substituted $C_3$-$C_8$ alkenyloxy group, wherein any —$CH_2$— in $R_4$ may be replaced by cyclopentyl, cyclobutyl or cyclopropyl;

(F) represents H or F; and $X_1$ and $X_2$ each independently represent H or F, but $X_1$ and $X_2$ are neither H at the same time nor F at the same time.

Preferably, the structural formula of said compound of structural formula IV is specifically at least one of formulas IV-1 to IV-13 below:

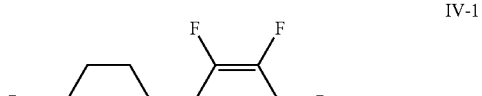
IV-1

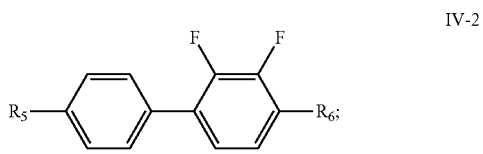
IV-2

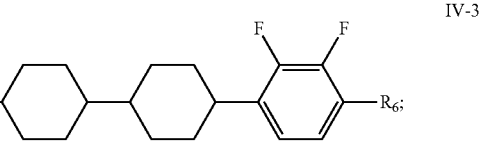
IV-3

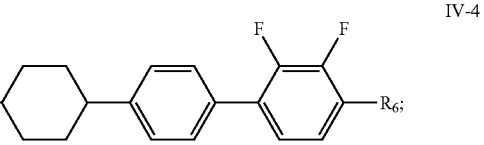
IV-4

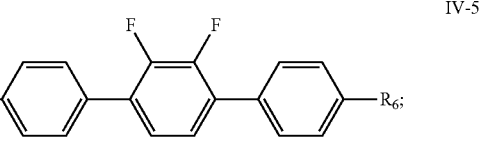
IV-5

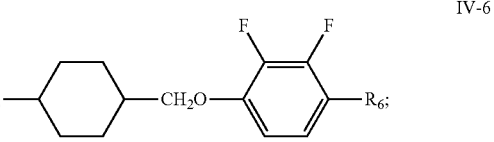
IV-6

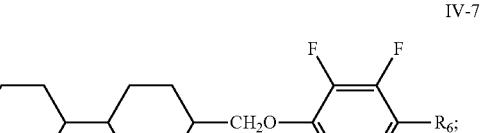
IV-7

IV-8

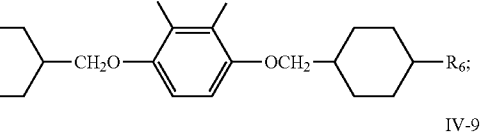
IV-9

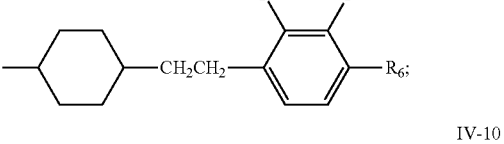
IV-10

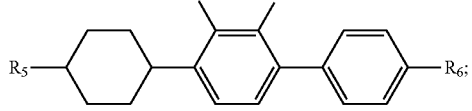

-continued

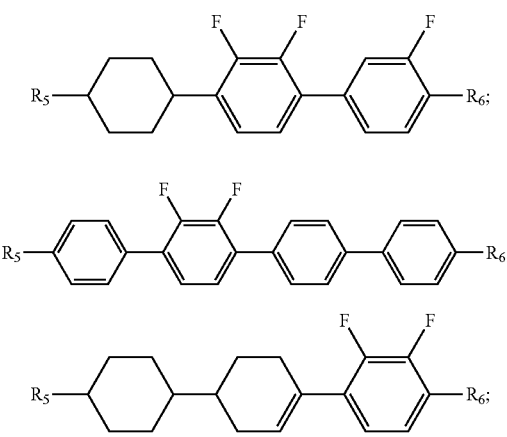

wherein

R$_5$ and R$_6$ each independently represent H, a C$_1$-C$_{10}$ alkyl group, a fluorine-substituted C$_1$-C$_{10}$ alkyl group, a C$_1$-C$_{10}$ alkoxy group, a fluorine-substituted C$_1$-C$_{10}$ alkoxy group, a C$_2$-C$_{10}$ alkenyl group, a fluorine-substituted C$_2$-C$_{10}$ alkenyl group, a C$_3$-C$_8$ alkenyloxy group or a fluorine-substituted C$_3$-C$_8$ alkenyloxy group, wherein any one of —CH$_2$— in R$_5$ and R$_6$ may be replaced by cyclopentyl, cyclobutyl or cyclopropyl.

Preferably, said liquid crystal medium further comprises one or more compounds of structural formula V and/or structural formula VI:

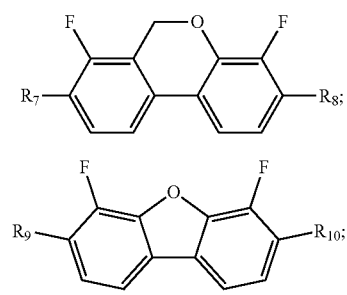

wherein

R$_7$, R$_8$, R$_9$ and R$_{10}$ each independently represent H, F, a C$_1$-C$_{10}$ alkyl group, a fluorine-substituted C$_1$-C$_{10}$ alkyl group, a C$_1$-C$_{10}$ alkoxy group, a fluorine-substituted C$_1$-C$_{10}$ alkoxy group, a C$_2$-C$_{10}$ alkenyl group, a fluorine-substituted C$_2$-C$_{10}$ alkenyl group, a C$_3$-C$_8$ alkenyloxy group or a fluorine-substituted C$_3$-C$_8$ alkenyloxy group, wherein any one of —CH$_2$— in R$_5$ and R$_6$ may be replaced by cyclopentyl, cyclobutyl or cyclopropyl.

Preferably, in the above-mentioned liquid crystal medium, the content in percentage by weight of the polymerizable compound of structural formula I is 0.001-5%, and the content in percentage by weight of the one or more compounds of structural formulas II-1 to II-12 or the one or more compounds of structural formula III is 0-70%.

More preferably, in the above-mentioned liquid crystal medium, the content in percentage by mass of the polymerizable compound of structural formula I is 0.05-2%, the content in percentage by mass of the one or more compounds of structural formulas II-1 to II-10 is 1-60%, and the content in percentage by mass of the one or more compounds of structural formula formulas II-11 and II-12 is 0-30%; wherein in formula II-11, R0 and R1 each independently represent a C$_1$-C$_5$ alkyl group or a C$_2$-C$_5$ alkenyl group; and in formula II-12, R2 and R3 each independently represent a C$_1$-C$_5$ alkyl group or a C$_1$-C$_5$ alkoxy group.

More preferably, in the above-mentioned liquid crystal medium, the content in percentage by mass of the polymerizable compound of structural formula I is 0.1-1%, the content in percentage by mass of the compound of structural formula III is 0-40%, the content in percentage by mass of the compound of structural formula IV is 1-90%, the content in percentage by mass of the compound of structural formula V is 0-20%, and the content in percentage by mass of the compound of structural formula VI is 0-30%.

More preferably, the structure of said compound of structural formula is specifically

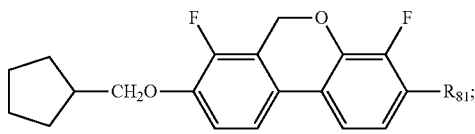

wherein R$_{81}$ represents an alkoxy group having a carbon atom number of 1-10.

Preferably, in the liquid crystal medium of the present invention, a chiral agent may be further added. An exemplary chiral agent may be a levorotatory or dextrorotatory structure, more preferably one or more of the following substances:

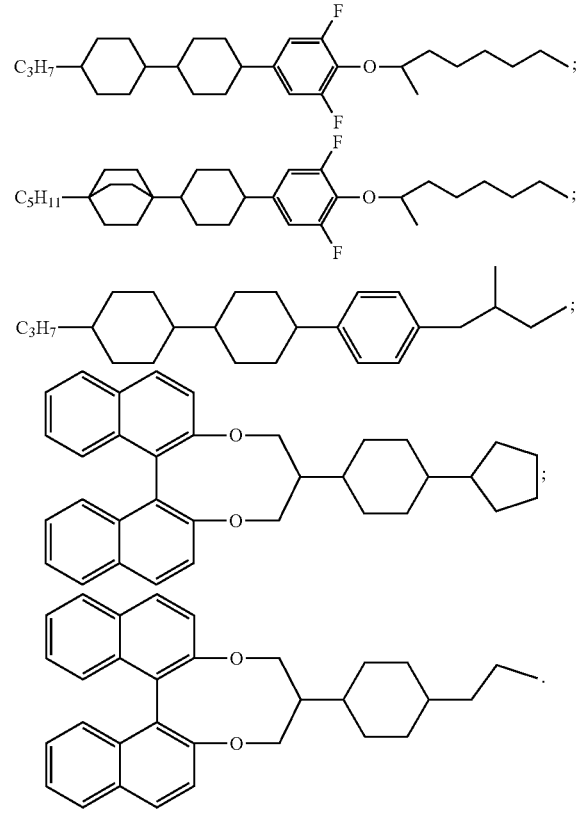

In the present invention, the liquid crystal media in different ratios of components will exhibit slightly different properties, such as a dielectric anisotropy Δε, an optical anisotropy Δn, a transition temperature point CP when the nematic phase of the liquid crystal transforms into a liquid, stability at low temperatures, which all may be different, and can be used in different types of display devices, but have the same characteristic that the rotary viscosities γ1 thereof are lower. The application to liquid crystal display devices can achieve a fast response.

In order to achieve the third objective as described above, the present invention provides a liquid crystal display device, which is prepared from the liquid crystal medium as described above.

Preferably, said liquid crystal display device is an active matrix display device or a passive matrix display device.

More preferably, said liquid crystal display device is an active matrix addressing liquid crystal display device.

Preferably, said liquid crystal display device is a VA-TFT or IPS-TFT liquid crystal display device.

Preferably, the liquid crystal medium of the present invention is particularly suitable for PS-(polymer stabilized) or PSA-(polymer stabilized alignment) type liquid crystal displays.

The present invention has the following beneficial effects:

The polymerizable compound of the present invention is a polymerizable mesogenic compound RM having two or more ring systems; especially, the differences from the conventional liquid crystal molecular rod structure are the specific molecular backbone thereof, the introduction of polymerizable groups P1 and P2 opposite to the direction of the long axis of the molecule and of substituent groups $Z_1$, $Z_2$, $S_1$ and $S_2$ into the molecular structure, and the entire molecular structure is curved and twisted. Surprisingly, in conjunction with the spatial effect, it is easier to carry out medium and low molecular weight agglomeration with an appropriate rate of polymerization, the polymer particles are uniform, the rate of defective liquid crystal display devices prepared from a liquid crystal medium containing the polymerizable compound is greatly reduced, the panel yield can be greatly increased and the difficulty of the panel process is reduced.

Furthermore, the liquid crystal medium further meets the well-known and acknowledged requirements, i.e., having a high stability to prevent demixing at low temperatures, a high resistivity, a wide operating temperature range, a short response time (even at low temperatures), a low threshold voltage (which makes a large amount of grey scale, a high contrast, and a wide viewing angle possible), and a high "voltage holding ratio" (HR) value after UV exposure.

BRIEF DESCRIPTION OF THE DRAWINGS

The particular embodiments of the present invention will be further described below in detail in conjunction with the drawings.

DETAILED DESCRIPTION OF EMBODIMENTS

Figure 1:
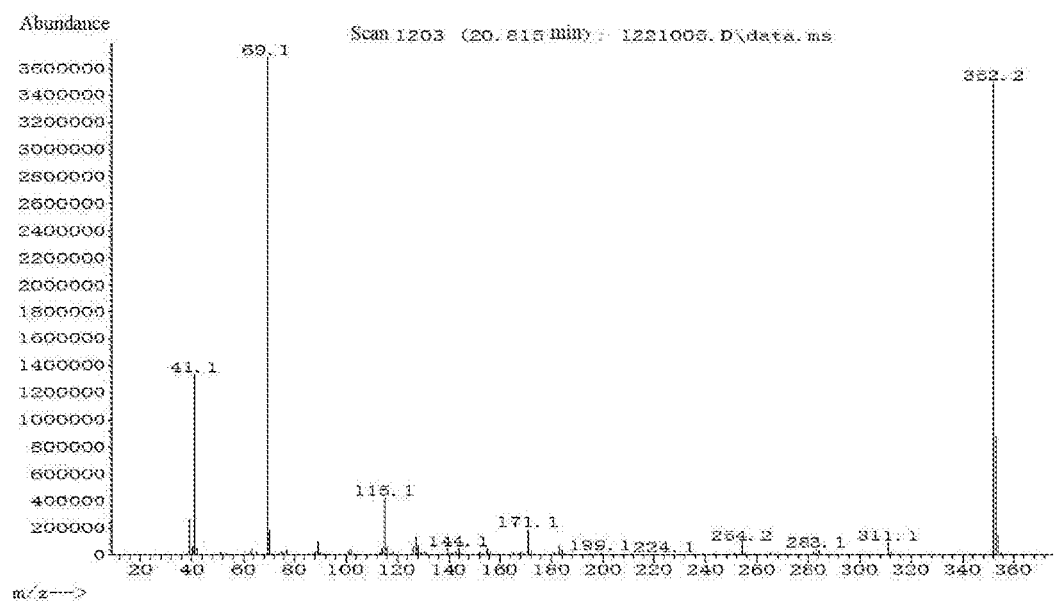
FIG. 1 shows a mass spectrum of a polymerizable compound of structural formula I-2-1 obtained in Example 2.

In order to more clearly illustrate the present invention, the present invention will be further described below in conjunction with preferred embodiments and the drawings. Similar parts in the drawings are denoted by the same reference numbers. A person skilled in the art should understand that the following contents described in detail are illustrative rather than limiting, and should not limit the scope of protection of the present invention.

In the present invention, preparation methods are all conventional methods unless otherwise specified. The raw materials used can all be available from open commercial approaches unless otherwise specified, and said percentages are all mass percentages unless otherwise specified.

In the present invention, compounds of structural formulas I to VI may all be referred to as liquid crystal monomers unless otherwise specified.

In the description of the present invention, the specific meaning of each symbol and the test conditions are as follows:

$C_P$ represents a liquid crystal clearing point (° C.), directly determined by WRX-1S microscopic thermal analyzer, with a temperature rate set to be 3° C./min;

Δn represents an optical anisotropy (589 nm, 20° C.);

Δε represents a dielectric anisotropy (25° C., 1 KHz, HP4284A, 5.2 micron TN levorotary box);

$γ_1$ represents a rotary viscosity (mPa·s) at 20° C.; VHR (%) represents a voltage holding ratio (5 V, 60 Hz, 20° C.); and ƒ(×1013 Ω·cm) represents a resistivity (20° C.); and testers for the voltage holding ratio VEER (%) and the electrical resistivity $ρ(×10^{13}$ Ω·cm) are both TOYO06254 and TOYO6517-type liquid crystal physical property evaluation systems (at a test temperature of 20° C., a time of 16 ms, and a test box of 7.0 microns).

In the present invention, the preparation of the polymerizable compound of structural formula I can be performed according to the following route:

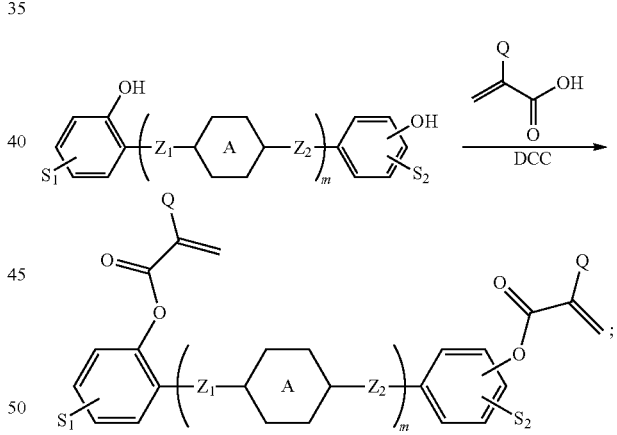

wherein Q represents H, an alkyl group, an alkoxy group, a fluorine-substituted alkyl group or a fluorine-substituted alkoxy group;

a person skilled in the art would be able to realise the preparation of the polymerizable compound of the present invention according to the description of the above-mentioned route. The reaction raw materials therein can all be synthesized by method known in the art or obtained commercial approaches. In addition, the reaction process of the preparation is generally monitored through TLC, and the post-treatments after the reaction is completed are generally water washing, extracting, combining organic phases and then drying, evaporating and removing the solvent under a reduced pressure, recrystallization and column chromatographic separation.

In the present invention, the equipment and instruments used for preparing the liquid crystal medium are:

(1) an electronic precision balance (with an accuracy of 0.1 mg)
(2) a stainless steel beaker for weighing a liquid crystal monomer;
(3) a spoon for adding a liquid crystal monomer;
(4) a magnetic rotor for stirring; and
(5) a temperature-controlled electromagnetic stirrer.

The method for preparing a liquid crystal medium comprises the following steps:

(1) monomers to be used are placed in order neatly;
(2) a stainless steel beaker is placed on the balance, and the liquid crystal monomers are placed into the stainless steel beaker with small spoons;
(3) the monomer liquid crystals are added in order by weights as required;
(4) the stainless steel beaker with the materials having been added is placed on the magnetic stirrer, heated and melted; and
(5) after most of the mixture in the stainless steel beaker is melted, a magnetic rotor is added to the stainless steel beaker to stir the liquid crystal mixture uniformly, and the mixture is cooled to room temperature to obtain the liquid crystal medium.

In order to more intuitively explain the structure of each component in the liquid crystal medium of the present invention, the structure of each component is denoted using a code, wherein the method for the code representation of ring structures, end groups and linking groups is shown in Table 1 and Table 2 below

TABLE 1

| Corresponding code for ring structure | |
|---|---|
| Cyclic structure | Corresponding code |
| (cyclohexane) | C |
| (cyclohexene) | L |
| (benzene) | B |
| (3-fluorobenzene) | B(3F) |
| (3,5-difluorobenzene) | B(3F,5F) |
| (2-fluorobenzene) | B(2F) |

TABLE 1-continued

| Corresponding code for ring structure | |
|---|---|
| Cyclic structure | Corresponding code |
| (2,3-difluorobenzene) | B(2F,3F) |
| (tetrahydropyran) | C[3O] |
| (dioxane) | C[3O,5O] |
| (fluorinated chroman) | Sa |
| (fluorinated dibenzofuran) | Df |

TABLE 2

| Corresponding code for end group and linking group | |
|---|---|
| End groups and linking groups | Corresponding code |
| $C_nH_{2n+1}$— | n- |
| $C_nH_{2n+1}O$— | nO— |
| —$OCF_3$ | —$OCF_3$ |
| —$CF_2O$— | —$CF_2O$— |
| —F | —F |
| —CN | —CN |
| —$CH_2CH_2$— | —E— |
| —CH=CH— | —V— |
| —C≡C— | —W— |
| —COO— | —COO— |
| —CH=CH—$C_nH_{2n+1}$ | Vn- |
| (cyclopentyl) | C(5)- |
| (cyclobutyl) | C(4)- |
| (cyclopropyl) | C(3)- |

For example:

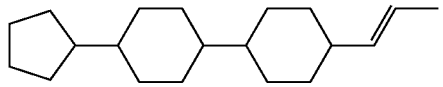

has a code of C(5)CCV1; and

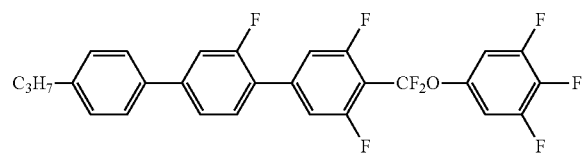

has a code of 3BB(3F)B(3F-5F)CF₂O B(3F,5F)F.

The following specific embodiments are used to illustrate the present invention:

Preparation of Polymerizable Compound

EXAMPLE 1

The structural formula of the polymerizable compound is as represented by the following formula I-1-1:

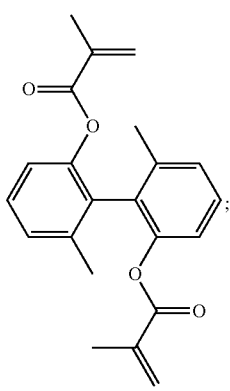

I-1-1 and
the route of the preparation thereof is as follows:

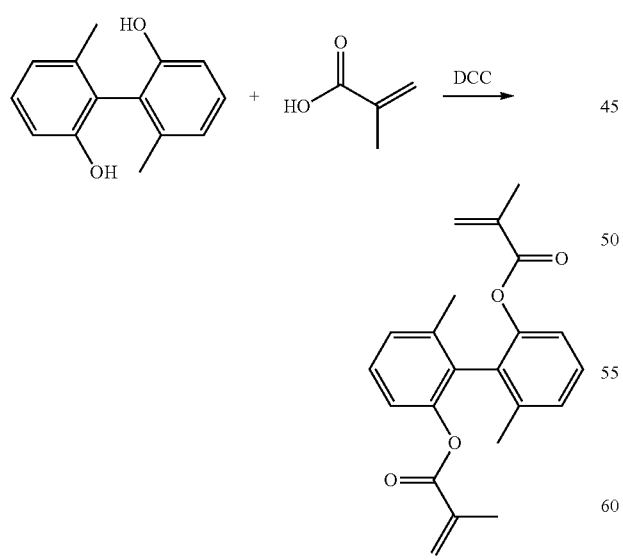

Specific operation procedures of the preparation:

To a 2 L three-necked flask, 0.1 mole of 6,6'-methyl-(1,1'-biphenyl)-2,2'-diphenol, 0.1 mole of methacrylic acid, and 0.5 L of toluene are charged, the temperature is reduced to 0° C. under the protection of nitrogen, the temperature is controlled at 0-5° C., 0.3 moles of DCC is added, and after the addition is complete, the temperature is naturally raised to room temperature (about 25° C.) for reactions for 8 hours. 500 ml of water is added, liquid separation is carried out, the aqueous phase is extracted with 100 ml×2 of toluene, the organic phases are combined and washed with 500 ml×2 of a saline solution, after the washing is complete, the organic phase is dried with anhydrous sodium sulphate and evaporated to dryness, 30 g of silica gel and 3 folds of petroleum ether (90-120° C.) are taken for passing a column, the column is rinsed with 2 folds of petroleum ether (90-120° C.), and after evaporation, 2 folds of ethanol is used for recrystallisation to obtain 20 g, with GC: 99.5% and yield: 63%.

EXAMPLE 2

The structural formula of the polymerizable compound is as represented by the following formula I-2-1:

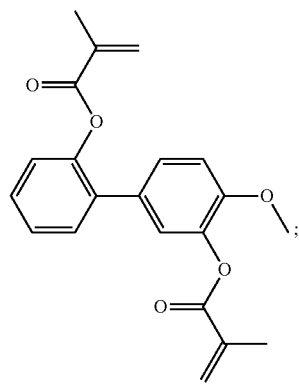

I-2-1 the route of the preparation thereof is as follows:

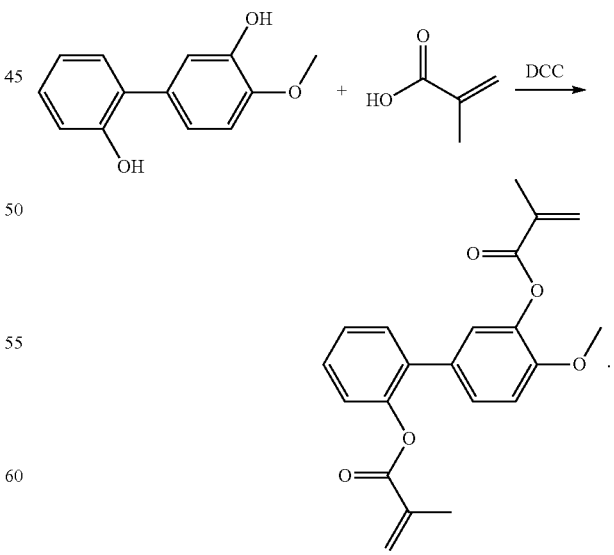

Specific operation procedures of the preparation:

To a 2 L three-necked flask, 0.1 mole of 4'-methoxy-(1,1'-biphenyl)-2,3'-diphenol, 0.1 mole of methacrylic acid, and 0.5 L of toluene are charged, the temperature is reduced to 0° C. under the protection of nitrogen, the temperature is controlled at 0-5° C., 0.3 moles of DCC is added, and after the addition is complete, the temperature is naturally raised to room temperature (about 25° C.) for reactions for 8 hours. 500 ml of water is added, liquid separation is carried out, the aqueous phase is extracted with 100 ml×2 of toluene, the organic phases are combined and washed with 500 ml×2 of a saline solution, after the washing is complete, the organic phase is dried with anhydrous sodium sulphate and evaporated to dryness, 30 g of silica gel and 3 folds of petroleum ether (90-120° C.) are taken for passing a column, the column is rinsed with 2 folds of petroleum ether (90-120° C.), and after evaporation, 2 folds of ethanol is used for recrystallisation to obtain 25 g, with GC: 99.7% and yield: 70%. The mass spectrum of the resulting compound of formula 1-2-1 is as shown in FIG. 1.

EXAMPLE 3

The structural formula of the polymerizable compound is as represented by the following formula I-3-1:

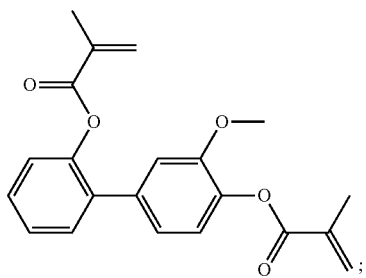

I-3-1 the route of the preparation thereof is as follows:

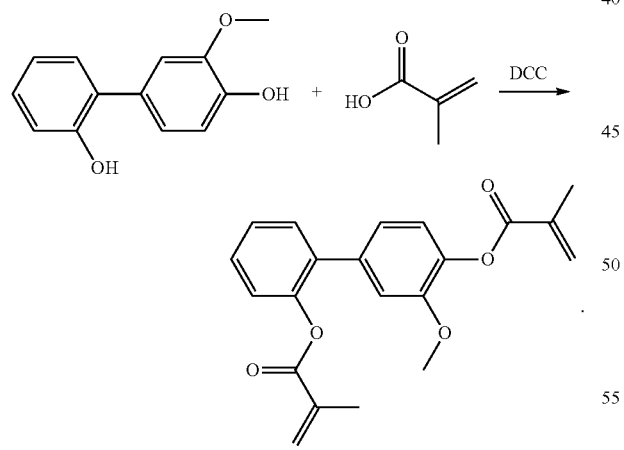

Specific operation procedures of the preparation:

To a 2 L three-necked flask, 0.1 mole of 3'-methoxy-(1,1'-biphenyl)-2,4'-diphenol, 0.1 mole of methacrylic acid, and 0.5 L of toluene are charged, the temperature is reduced to 0° C. under the protection of nitrogen, the temperature is controlled at 0-5° C., 0.3 moles of DCC is added, and after the addition is complete, the temperature is naturally raised to room temperature (about 25° C.) for reactions for 8 hours. 500 ml of water is added, liquid separation is carried out, the aqueous phase is extracted with 100 ml×2 of toluene, the organic phases are combined and washed with 500 ml×2 of a saline solution, after the washing is complete, the organic phase is dried with anhydrous sodium sulphate and evaporated to dryness, 30 g of silica gel and 3 folds of petroleum ether (90-120° C.) are taken for passing a column, the column is rinsed with 2 folds of petroleum ether (90-120° C.), and after evaporation, 2 folds of ethanol is used for recrystallisation to obtain 25g, with GC: 99.7% and yield: 70%.

EXAMPLE 4

The structural formula of the polymerizable compound is as represented by the following formula I-4-1:

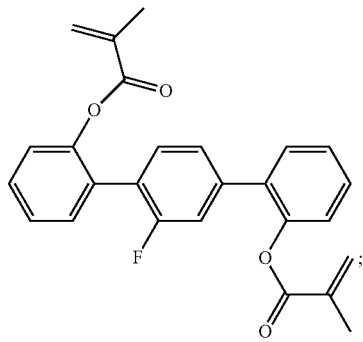

I-4-1 the route of the preparation thereof is as follows:

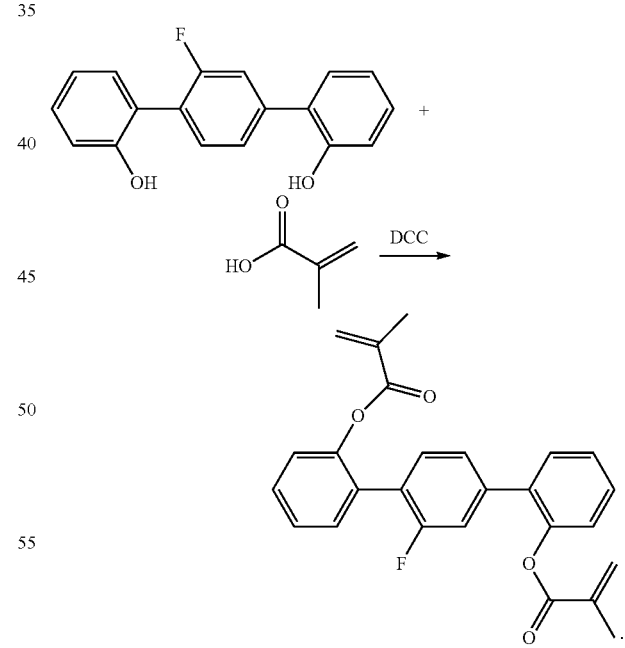

Figure 2:
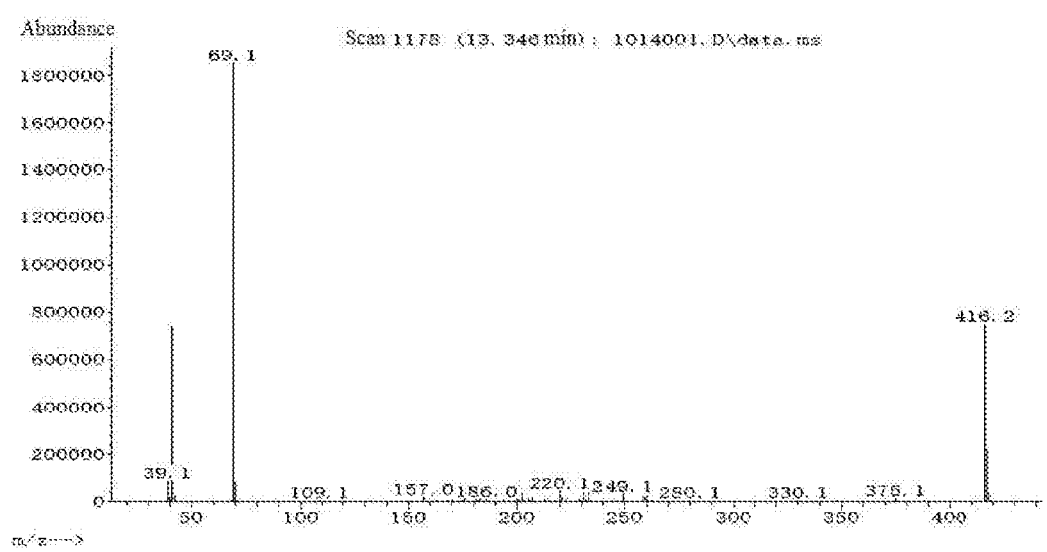
FIG. 2 shows a mass spectrum of a polymerizable compound of structural formula I-4-1 obtained in Example 4.

Specific operation procedures of the preparation:

To a 2 L three-necked flask, 0.1 mole of 2'-fluoro-(1,1':4',1"-terphenyl)-2,2"-diphenol, 0.1 mole of methacrylic acid, and 1 L of toluene are charged, the temperature is reduced to 0° C. under the protection of nitrogen, the temperature is controlled at 0-5° C., 0.3 moles of DCC is added, and after the addition is complete, the temperature is naturally raised to room temperature (about 25° C.) for reactions for 8 hours. 500 ml of water is added, liquid separation is carried out, the aqueous phase is extracted with 200 ml×2 of toluene, the organic phases are combined and washed with 500 ml×2 of a saline solution, after the washing is complete, the organic phase is dried with anhydrous sodium sulphate and evaporated to dryness, 50 g of silica gel and 5 folds of petroleum ether (90-120° C.) are taken for passing a column, the column is rinsed with 2 folds of petroleum ether (90-120° C.), and after evaporation, 2 folds of ethanol and 0.5 folds of toluene are used for recrystallisation to obtain 27 g, with GC: 99.6% and yield: 65%. The mass spectrum of the resulting compound of formula I-4-1 is as shown in FIG. 2.

EXAMPLE 5

The structural formula of the polymerizable compound is as represented by the following formula I-5-1:

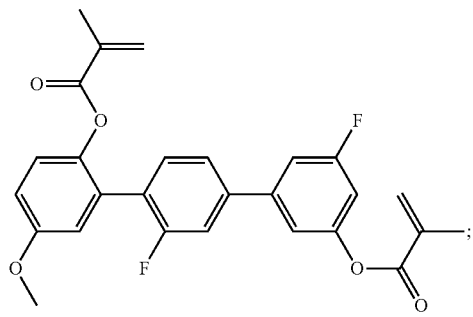

I-5-1 the route of the preparation thereof is as follows:

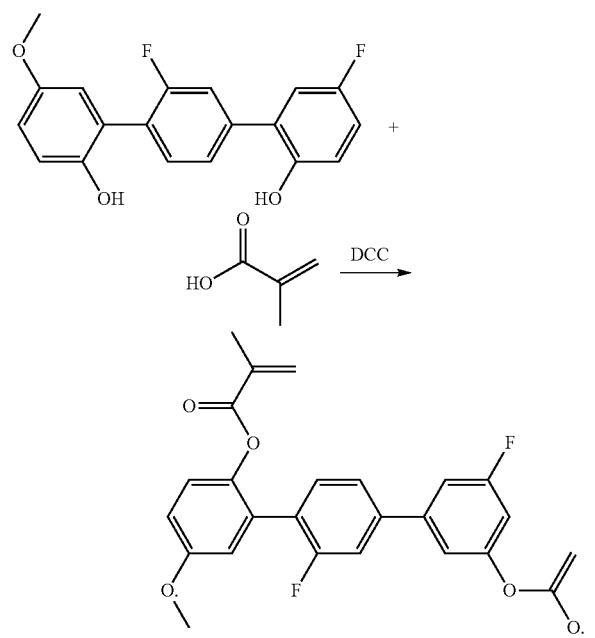

Specific operation procedures of the preparation:
To a 2 L three-necked flask, 0.1 mole of 2',5''-difluoro-5-methoxy-(1,1':4',1''-terphenyl)-2,2''-diphenol, 0.1 mole of methacrylic acid, and 1 L of toluene are charged, the temperature is reduced to 0° C. under the protection of is nitrogen, the temperature is controlled at 0-5° C., 0.3 moles of DCC is added, and after the addition is complete, the temperature is naturally raised to room temperature (about 25° C.) for reactions for 8 hours. 500 ml of water is added, liquid separation is carried out, the aqueous phase is extracted with 200 ml×2 of toluene, the organic phases are combined and washed with 500 ml×2 of a saline solution, after the washing is complete, the organic phase is dried with anhydrous sodium sulphate and evaporated to dryness, 50 g of silica gel and 5 folds of petroleum ether (90-120° C.) are taken for passing a column, the column is rinsed with 2 folds of petroleum ether (90-120° C.), and after evaporation, 2 folds of ethanol and 0.5 folds of toluene are used for recrystallisation to obtain 30 g, with GC: 99.6% and yield: 65%.

EXAMPLE 6

The structural formula of the polymerizable compound is as represented by the following formula I-6-1:

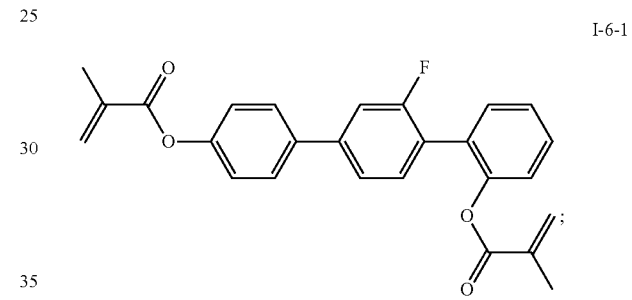

I-6-1 the route of the preparation thereof is as follows:

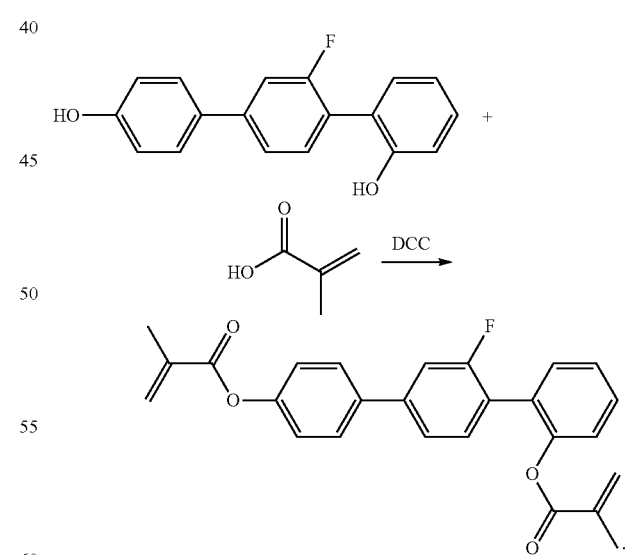

Figure 3:
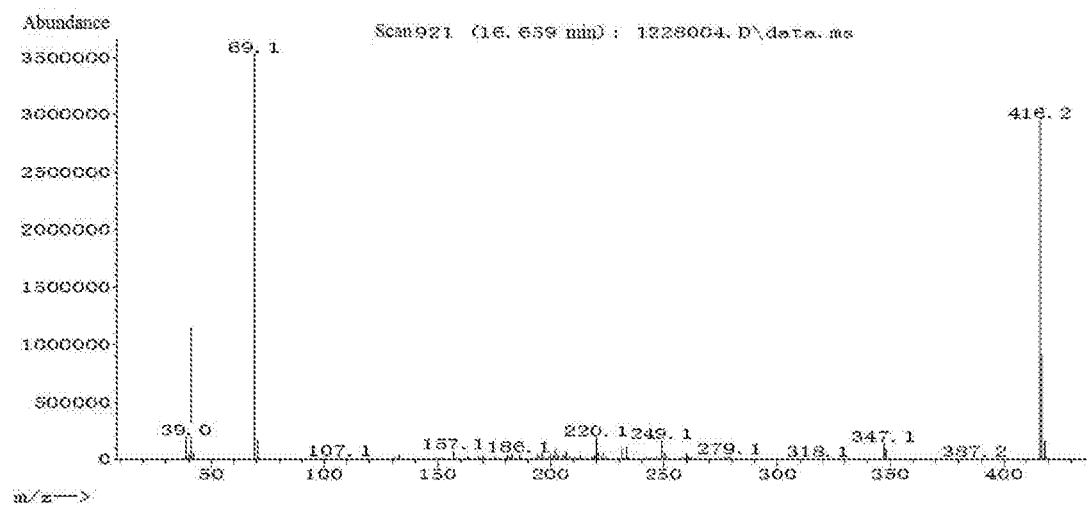
FIG. 3 shows a mass spectrum of a polymerizable compound of structural formula I-6-1 obtained in Example 6.

Specific operation procedures of the preparation:
To a 2 L three-necked flask, 0.1 mole of 2'-fluoro-(1,1.': 4',1''-terphenyl)-2,4''-diphenol, 0.1 mole of methacrylic acid, and 1 L of toluene are charged, the temperature is reduced to 0° C. under the protection of nitrogen, the temperature is controlled at 0-5° C., 0.3 moles of DCC is added, and after the addition is complete, the temperature is naturally raised to room temperature (about 25° C.) for reactions for 8 hours. 500 ml of water is added, liquid separation is carried out, the aqueous phase is extracted with 200 ml×2 of toluene, the organic phases are combined and washed with 500 ml×2 of a saline solution, after the washing is complete, the organic phase is dried with anhydrous sodium sulphate and evaporated to dryness, 50g of silica gel and 5 folds of petroleum ether (90-120° C.) are taken for passing a column, the column is rinsed with 2 folds of petroleum ether (90-120° C.), and after evaporation, 2 folds of ethanol and 0.5 folds of toluene are used for recrystallisation to obtain 28g, with GC: 99.9% and yield: 69%. The mass spectrum of the resulting compound of formula I-6-1 is as shown in FIG. 3.

EXAMPLE 7

The structural formula of the polymerizable compound is as represented by the following formula I-1-2:

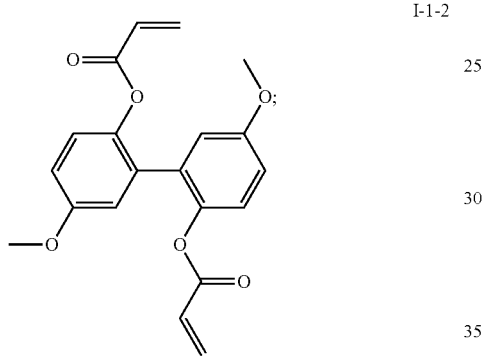

I-1-2 the route of the preparation t is as follows:

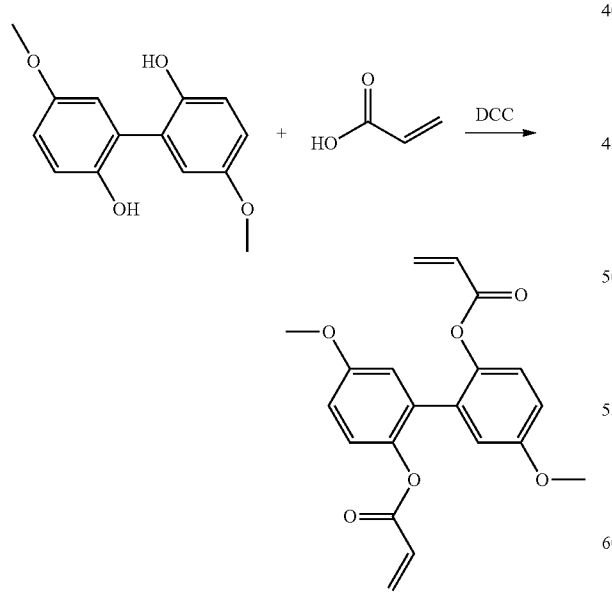

Specific operation procedures of the preparation:

To a 2 L three-necked flask, 0.1 mole of 4,4'-methoxy-(1,1'-biphenyl)-2,2'-diphenol, 0.1 mole of acrylic acid, and 0.5 L of toluene are charged, the temperature is reduced to 0° C. under the protection of nitrogen, the temperature is controlled at 0-5° C., 0.3 moles of DCC is added, and after the addition is complete, the temperature is naturally raised to room temperature (about 25° C.) for reactions for 8 hours. 500 ml of water is added, liquid separation is carried out, the aqueous phase is extracted with 100 ml×2 of toluene, the organic phases are combined and washed with 500 ml×2 of a saline solution, after the washing is complete, the organic phase is dried with anhydrous sodium sulphate and evaporated to dryness, 30 g of silica gel and 3 folds of petroleum ether (90-120° C.) are taken for passing a column, the column is rinsed with 2 folds of petroleum ether (90-120° C.), and after evaporation, 2 folds of ethanol is used for recrystallisation to obtain 17.6 g, with GC: 99,6% and yield: 60%.

EXAMPLE 8

The structural formula of the polymerizable compound is as represented by the following formula I-2-2:

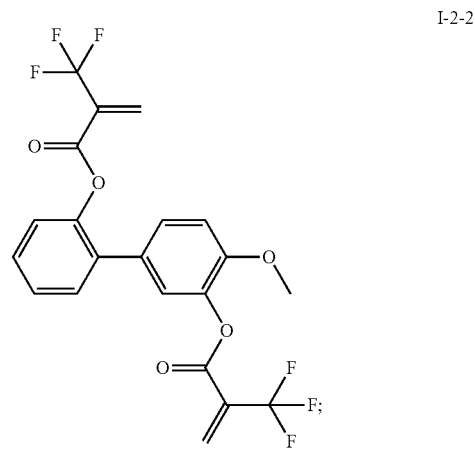 [SMILES: C=C(C(=O)Oc1cc(-c2ccccc2OC(=O)C(=C)C(F)(F)F)ccc1OC)C(F)(F)F]

I-2-2 the route of the preparation thereof is as follows:

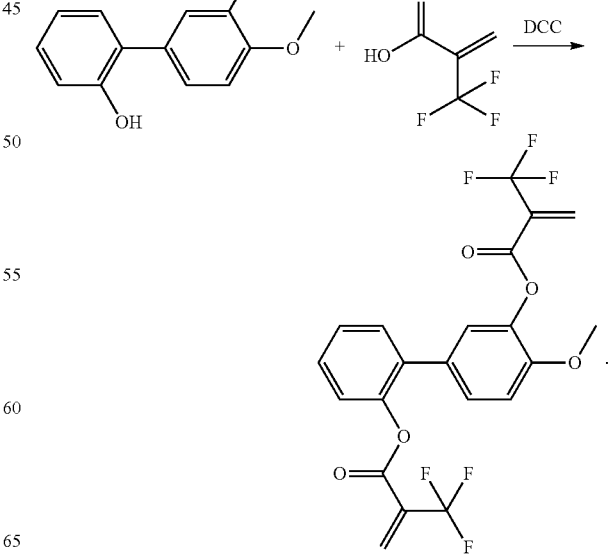

Specific operation procedures of the preparation:

To a 2 L three-necked flask, 0.1 mole of 4'-methoxy-(1,1'-biphenyl)-2,3'-diphenol, 0.5 moles of trifluoromethacrylic acid, and 0.5 L of toluene are charged, the temperature is reduced to 0° C. under the protection of nitrogen, the temperature is controlled at 0-5° C., 0.3 moles of DCC is added, and after the addition is complete, the temperature is naturally raised to room temperature (about 25° C.) for reactions for 8 hours. 500 ml of water is added, liquid separation is carried out, the aqueous phase is extracted with 100 ml×2 of toluene, the organic phases are combined and washed with 500 ml×2 of a saline solution, after the washing is complete, the organic phase is dried with anhydrous sodium sulphate and evaporated to dryness, 30 g of silica gel and 3 folds of petroleum ether (90-120° C.) are taken for passing a column, the column is rinsed with 2 folds of petroleum ether (90-120° C.), and after evaporation, 2 folds of ethanol is used for recrystallisation to obtain 13.8g, with GC: 99.1% and yield: 30%.

EXAMPLE 9

The structural formula of the polymerizable compound is as represented by the following formula I-3-2:

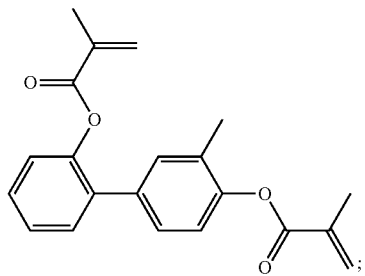

I-3-2 the route of the preparation thereof is as follows:

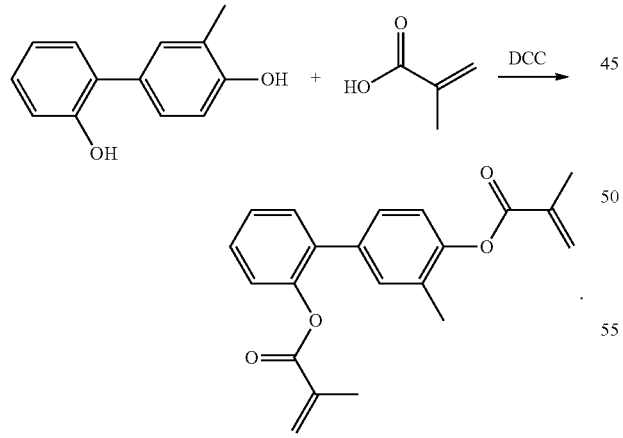

Specific operation procedures of the preparation:

To a 2 L three-necked flask, 0.1 mole of 3'-methyl-(1,1'-biphenyl)-2,4'-diphenol, 0.1 mole of methacrylic acid, and 0.5 L of toluene are charged, the temperature is reduced to 0° C. under the protection of nitrogen, the temperature is controlled at 0-5° C., 0.3 moles of DCC is added, and after the addition is complete, the temperature is naturally raised to room temperature (about 25° C.) for reactions for 8 hours. 500 ml of water is added, liquid separation is carried out, the aqueous phase is extracted with 100 ml×2 of toluene, the organic phases are combined and washed with 500 ml×2 of a saline solution, after the washing is complete, the organic phase is dried with anhydrous sodium sulphate and evaporated to dryness, 30 g of silica gel and 3 folds of petroleum ether (90-120° C.) are taken for passing a column, the column is rinsed with 2 folds of petroleum ether (90-120° C.), and after evaporation, 2 folds of ethanol is used for recrystallisation to obtain 16.8 g, with GC: 99.7% and yield: 50%.

EXAMPLE 10

The structural formula of the polymerizable compound is as represented by the following formula I-4-2:

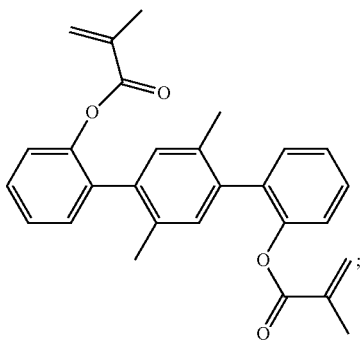

I-4-2 the route of the preparation thereof is as follows:

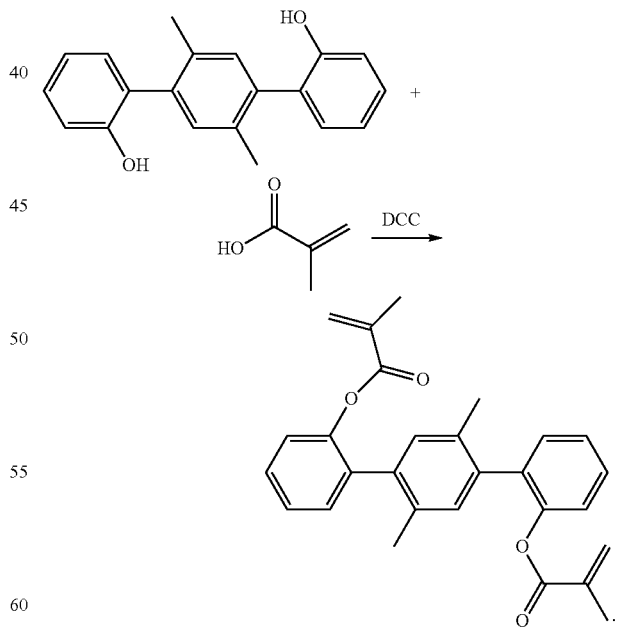

Specific operation procedures of the preparation:

To a 2 L three-necked flask, 0.1 mole of 2',2'-dimethyl-(1,1':4',1"-terphenyl)-2,2"-diphenol, 0.1 mole of methacrylic acid, and 1 L of toluene are charged, the temperature is reduced to 0° C. under the protection of nitrogen, the temperature is controlled at 0-5° C., 0.3 moles of DCC is added, and after the addition is complete, the temperature is naturally raised to room temperature (about 25° C.) for reactions for 8 hours. 500 ml of water is added, liquid separation is carried out, the aqueous phase is extracted with 200ml×2 of toluene, the organic phases are combined and washed with 500 ml×2 of a saline solution, after the washing is complete, the organic phase is dried with anhydrous sodium sulphate and evaporated to dryness, 50 g of silica gel and 5 folds of petroleum ether (90-120° C.) are taken for passing a column, the column is rinsed with 2 folds of petroleum ether (90-120° C.), and after evaporation, 2 folds of ethanol and 0.5 folds of toluene are used for recrystallisation to obtain 27.6 g, with GC: 99.6% and yield: 65%.

EXAMPLE 11

The structural formula of the polymerizable compound is as represented by the following formula I-5-2:

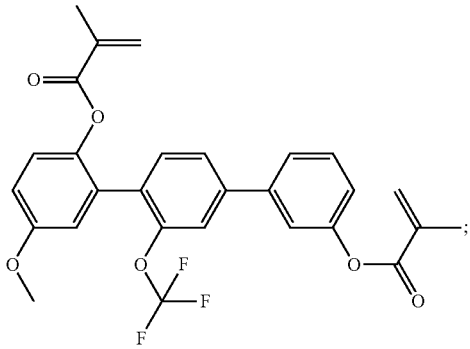

I-5-2 the route of the preparation thereof is as follows:

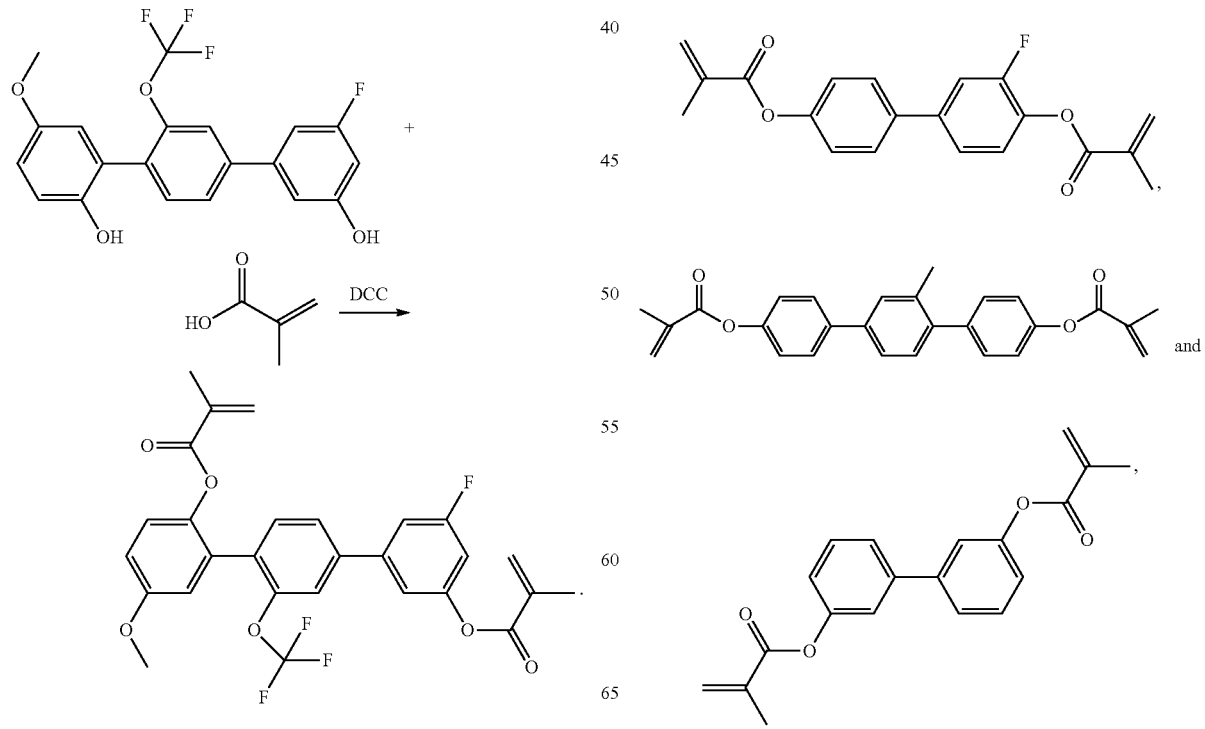

Specific operation procedures of the preparation:

To a 2 L three-necked flask, 0.1 mole of 2',5"-difluoro-5-methoxy-(1,1':4',1"-terphenyl)-2,2"-diphenol, 0.1 mole of methacrylic acid, and 1 L of toluene are charged, the temperature is reduced to 0° C. under the protection of nitrogen, the temperature is controlled at 0-5° C., 0.3 moles of DCC is added, and after the addition is complete, the temperature is naturally raised to room temperature (about 25° C.) for reactions for 8 hours. 500 ml of water is added, liquid separation is carried out, the aqueous phase is extracted with 200 ml×2 of toluene, the organic phases are combined and washed with 500 ml×2 of a saline solution, after the washing is complete, the organic phase is dried with anhydrous sodium sulphate and evaporated to dryness, 50 g of silica gel and 5 folds of petroleum ether (90-120° C.) are taken for passing a column, the column is rinsed with 2 folds of petroleum ether (90-120° C.), and after evaporation, 2 folds of ethanol and 0.5 folds of toluene are used for recrystallisation to obtain 33 g, with GC: 99.6% and yield: 65%.

Determination of the Rate of Polymerization of a Liquid Crystal Medium Prepared from a Polymerizable Compound in a Liquid Crystal Display Device:

with a mixture of the compounds of formulas II to IV as described in Table 3 as mother MUTY, and 3000 ppm of the polymerizable compound RMs of Examples 1-6 are respectively added thereto; for comparison, equivalent amounts of

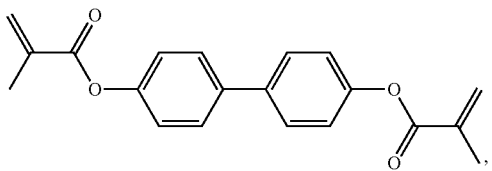

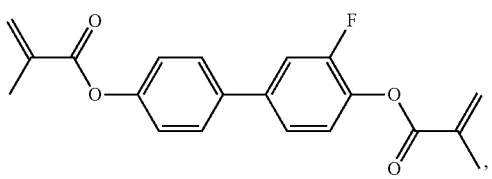

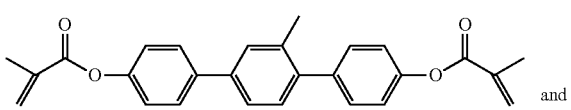

and

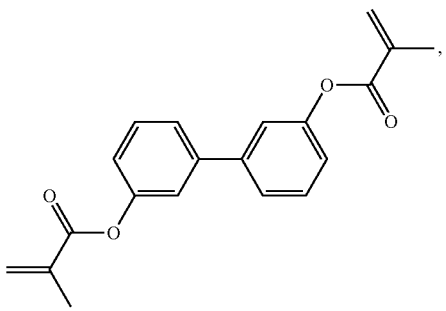

-continued

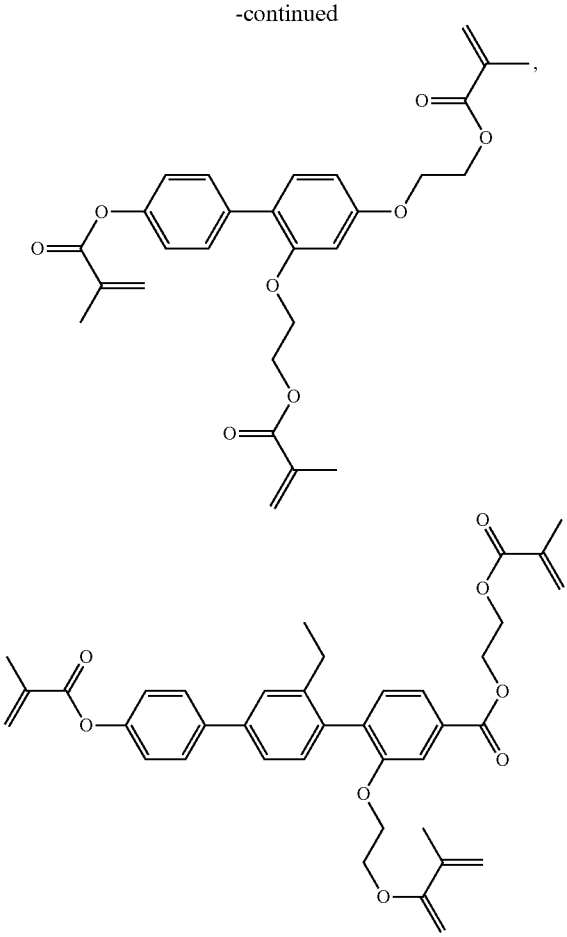

are respectively added to MUTY, liquid crystal media are prepared by the is above-mentioned liquid crystal medium preparation method, the liquid crystal media are filled into liquid crystal cells, the PSA panel process is simulated, and the rate of polymerization thereof is determined, with the specific conditions being: UV1:80 mW/cm$^2$@365 nm, 200 s; UV2:5 mW/cm$^2$@365 nm, 120 min, and the liquid crystal cells are further cut open for HPLC analysis, with the results being as shown in Table 4 below.

TABLE 3

Code and amount of each compound in MUTY

| Category of compound structural formula | Compound code | Percentage by mass (%) |
|---|---|---|
| II | 3CC2 | 16 |
| III | 3CCB1 | 6 |
| III | 2CCB1 | 6 |
| II | 1BB5 | 8 |
| II | 5CB3 | 6 |
| III | 3CCB 2 | 6 |
| III | 3CBB2 | 5 |
| IV | 3CB(2F,3F)O2 | 8 |
| IV | 3BB(2F,3F)O2 | 17 |
| IV | 3C1OB(2F,3F)O2 | 6 |
| IV | 3CCB(2F,3F)O4 | 5 |
| IV | 2CBB(2F,3F)O2 | 11 |

TABLE 4

Residues of polymerizable compound RMs at different UV irradiation times

| Sample composition | RM residue at different UV irradiation times | | | |
|---|---|---|---|---|
|  | 0 min | 20 min | 40 min | 60 min |
| MUTY + I-1-1 | 3022 | 1516 | 758 | 501 |
| MUTY + I-2-1 | 3015 | 1423 | 730 | 480 |
| MUTY + I-3-1 | 3016 | 1520 | 765 | 498 |
| MUTY + I-4-1 | 3014 | 1631 | 930 | 510 |
| MUTY + I-5-1 | 3015 | 1631 | 950 | 520 |
| MUTY + I-6-1 | 3020 | 1211 | 690 | 410 |
| MUTY + (structure) | 2072 | 1033 | 581 | 478 |
| MUTY + (structure) | 2368 | 1271 | 897 | 617 |

TABLE 4-continued
Residues of polymerizable compound RMs at different UV irradiation times
| Sample composition | RM residue at different UV irradiation times | | | |
|---|---|---|---|---|
| | 0 min | 20 min | 40 min | 60 min |
| MUTY + 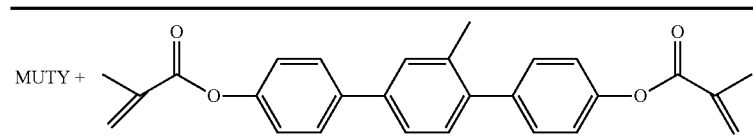 | 1169 | 398 | 200 | 121 |
| MUTY + 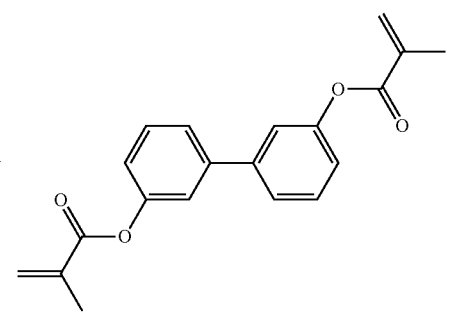 | 3020 | 1718 | 897 | 750 |
| MUTY + 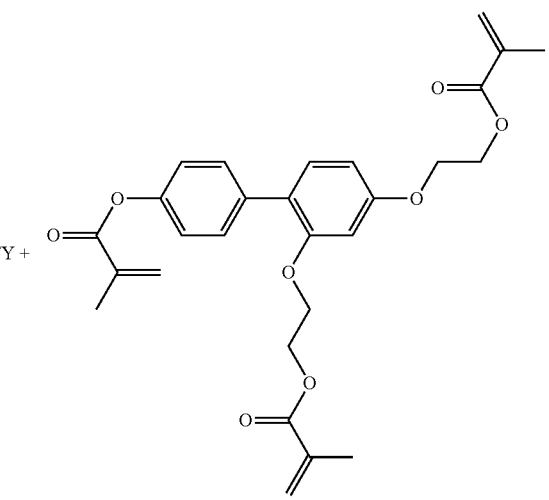 | 3010 | 1908 | 987 | 850 |
| MUTY + 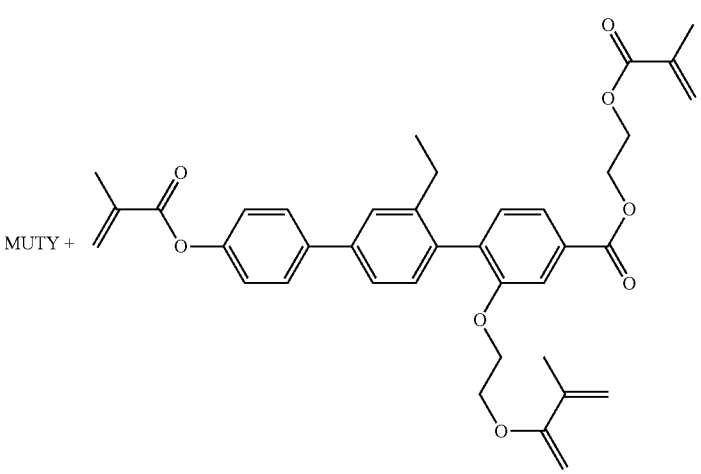 [SMILES: C=C(C)C(=C)OCCOc1cc(C(=O)OCCOC(=O)C(=C)C)ccc1-c1ccc(-c2ccc(OC(=O)C(=C)C)cc2)cc1CC] | 3005 | 1818 | 899 | 730 |

It can be seen from Table 4 above that with respect to compounds

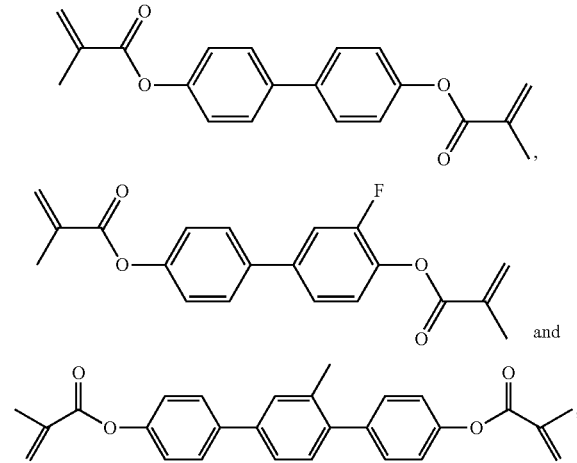

the polymerizable compound RM provided in the present invention has a better intermiscibility with the mother MUTY mixture, the solubility thereof is higher, which is beneficial to increase the degree of coverage of a film resulting from RM polymerization, the alignment ability of an alignment layer is improved, and the mixture has a more excellent low-temperature stability. Compared with

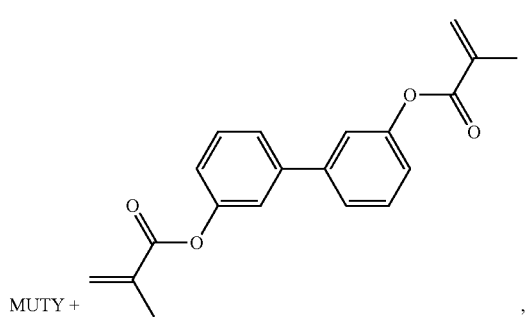

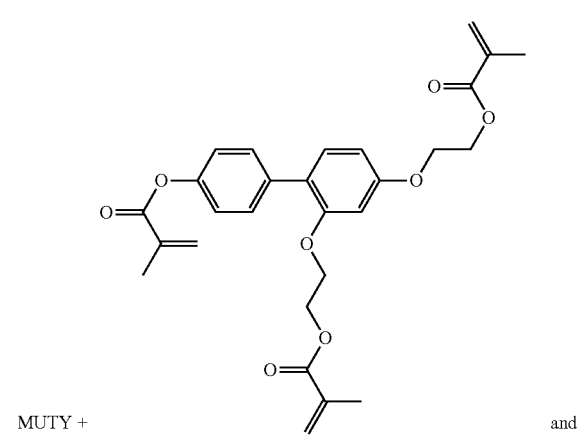

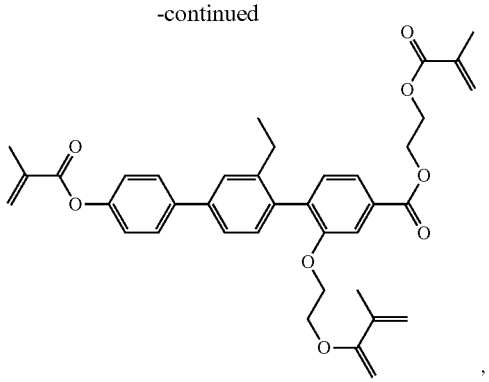

the rate of polymerization conversion of RM thereof in the same UV process is closer to that of

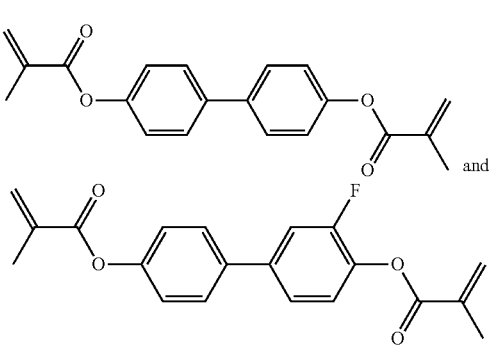

of the current mainstream technologies, and the formed polymer alignment layer has a more uniform particle size, effectively preventing the occurrence of defects. In additon, with regard to the technical solution of MUTY + [structure], since the rate of polymerization is too high, large particle polymers are easily formed, easily causing defects such as zara particles. Compared with the prior art, the present invention has greater advantages, cannot be inferred through the prior art, is a huge improvement over the prior art, and thus provides a better protection for TFT displays that require higher and higher reliability of mixed liquid crystals.

Preparation of Liquid Crystal Medium:

EXAMPLES 12-26

The formulations of Examples 12-26 are respectively as shown in Tables 5-19 below, wherein in Tables 5-19, compounds having structural formulas II to VI other than polymerizable compounds having structural formula I are used as nematic phases, the sum of the nematic phase content being 100%, and then polymerizable compounds of structural formula I having specific contents are added to the nematic phases to prepare liquid crystal media.

The resulting liquid crystal media are filled in between two substrates of a liquid crystal display for performance testing, and the test results are also respectively listed in Tables 5-19.

TABLE 5

Structure type, code and content of the raw material compound of a liquid crystal medium prepared in Example 12 and the performance of the liquid crystal medium

| Category of compound structural formula | Compound code | Percentage by mass (%) |
|---|---|---|
| II | 3CC2 | 16 |
| III | 3CCB1 | 6 |
| III | 2CCB1 | 6 |
| II | 1BB5 | 8 |
| II | 5CB3 | 6 |
| III | 3CCB 2 | 6 |
| III | 3CBB2 | 5 |
| IV | 3CB(2F,3F)O2 | 8 |
| IV | 3BB(2F,3F)O2 | 17 |
| IV | 3C1OB(2F,3F)O2 | 6 |
| IV | 3CCB(2F,3F)O4 | 5 |
| IV | 2CBB(2F,3F)O2 | 11 |
| I | I-1-1 | 0.3 |
| Performance of liquid crystal medium | $\Delta\varepsilon$ [1 KHz, 20° C.]: −3.0; $\Delta$n[589 nm, 20° C.]: 0.109; Cp: 85° C.; and $\gamma_1$: 75 mPa · s. | |

TABLE 6

Structure type, code and content of the raw material compound of a liquid crystal medium prepared in Example 13 and the performance of the liquid crystal medium

| Category of compound structural formula | Compound code | Percentage by mass (%) |
|---|---|---|
| II | 3CC2 | 23 |
| II | 3CCV1 | 12 |
| III | 3CCB1 | 4 |
| III | 3CBB2 | 3 |
| III | 3CCB2 | 4 |
| III | 3CBB3 | 4 |
| IV | 2CCB(2F,3F)O2 | 9 |
| IV | 2CBB(2F,3F)O4 | 8 |
| III | V2CCB1 | 10 |
| IV | C(5)CBB(2F,3F)O4 | 7 |
| IV | 3CBB(2F,3F)O2 | 10 |
| V | C(5)1OSaO4 | 6 |
| I | I-2-1 | 1 |
| Performance of liquid crystal medium | $\Delta\varepsilon$ [1 KHz, 20° C.]: −3.2; $\Delta$n[589 nm, 20° C.]: 0.109; Cp: 72° C.; and $\gamma_1$: 70 mPa · s. | |

TABLE 7

Structure type, code and content of the raw material compound of a liquid crystal medium prepared in Example 14 and the performance of the liquid crystal medium

| Category of compound structural formula | Compound code | Percentage by mass (%) |
|---|---|---|
| II | 3CC2 | 20 |
| II | 3CCV | 18 |
| II | 5CB3 | 2 |
| III | V2CCB1 | 5 |
| III | VCCB1 | 5 |
| IV | 2CCB(2F,3F)O2 | 12 |
| IV | 2CBB(2F,3F)O2 | 8 |
| IV | C(3)1BB(2F,3F)O2 | 17 |

TABLE 7-continued

Structure type, code and content of the raw material compound of a liquid crystal medium prepared in Example 14 and the performance of the liquid crystal medium

| Category of compound structural formula | Compound code | Percentage by mass (%) |
|---|---|---|
| VI | 3ODfO4 | 6 |
| III | 3CBBC3 | 7 |
| I | I-3-1 | 0.5 |
| Performance of liquid crystal medium | $\Delta\varepsilon$ [1 KHz, 20° C.]: −3.5; $\Delta$n[589 nm, 20° C.]: 0.098; Cp: 75° C.; $\gamma_1$: 81 mPa · s. | |

TABLE 8

Structure type, code and content of the raw material compound of a liquid crystal medium prepared in Example 15 and the performance of the liquid crystal medium

| Category of compound structural formula | Liquid crystal monomer code | Percentage by mass (%) |
|---|---|---|
| II | 3CC2 | 30 |
| II | 3CCV | 20 |
| III | VCCB1 | 2 |
| III | V2CCB1 | 3 |
| III | 5BBB(2F,4F) | 13 |
| IV | C(3)1CBB(2F,3F)O2 | 17 |
| IV | C(5)CBB (2F,3F)O4 | 6 |
| VI | C(5) 1ODfO4 | 1 |
| V | C(5)1OSaO4 | 3 |
| VI | C(3) 1ODfO4 | 5 |
| I | I-4-1 | 0.2 |
| Performance of liquid crystal medium | $\Delta\varepsilon$ [1 KHz, 20° C.]: −4.1; $\Delta$n[589 nm, 20° C.]: 0.115; Cp: 72° C.; $\gamma_1$: 77 mPa · s. | |

TABLE 9

Structure type, code and content of the raw material compound of a liquid crystal medium prepared in Example 16 and the performance of the liquid crystal medium

| Category of compound structural formula | Compound code | Percentage by mass (%) |
|---|---|---|
| II | 3CC2 | 5 |
| II | 3CCV | 45 |
| III | 3CBB2 | 5 |
| III | 3CBB3 | 5 |
| III | C(3) 1BB(3F)B5 | 8 |
| IV | C(3) 1CBB(2F,3F)O2 | 5 |
| IV | C(3) 1CBB(2F,3F)O4 | 7 |
| IV | 3CC1OB(2F,3F)O2 | 6 |
| IV | 3CC1OB(2F,3F)O4 | 6 |
| IV | 3CBB(2F,3F)O2 | 3 |
| IV | 3CB (2F,3F)O2 | 5 |
| I | I-5-1 | 0.35 |
| Performance of liquid crystal medium | $\Delta\varepsilon$ [1 KHz, 20° C.]: −3.8; $\Delta$n[589 nm, 20° C.]: 0.11; Cp: 76° C.; and $\gamma_1$: 72 mPa · s. | |

TABLE 10

Structure type, code and content of the raw material compound of a liquid crystal medium prepared in Example 17 and the performance of the liquid crystal medium

| Category of compound structural formula | Compound code | Percentage by mass (%) |
|---|---|---|
| II | 3CC2 | 10 |
| III | 3CBB2 | 6 |
| III | 3CCB1 | 6 |
| II | 1BB5 | 8 |
| II | 5CB3 | 6 |
| III | C(3) 1BB(3F)B2 | 5 |
| III | 3CBB3 | 6 |
| IV | 3CBB(2F,3F)O2 | 8 |
| IV | 2CBB(2F,3F)O2 | 12 |
| IV | 3C1OB(2F,3F)O2 | 10 |
| IV | C(5)BB(2F,3F)O2 | 10 |
| III | 5BBB(2F,4F) | 13 |
| I | I-6-1 | 0.15 |
| Performance of liquid crystal medium | $\Delta\varepsilon$ [1 KHz, 20° C.]: −3.4; $\Delta n$[589 nm, 20° C.]: 0.12; Cp: 76° C.; and $\gamma_1$: 95 mPa · s. | |

TABLE 11

Structure type, code and content of the raw material compound of a liquid crystal medium prepared in Example 18 and the performance of the liquid crystal medium

| Category of compound structural formula | Liquid crystal monomer code | Percentage by mass (%) |
|---|---|---|
| II | 3CC2 | 23 |
| II | 3CCV1 | 12 |
| III | 5BBB(2F,4F) | 7 |
| III | 3BBB(2F,4F) | 7 |
| III | 2CBB2 | 9 |
| III | 3CBB2 | 5 |
| IV | 3CBB (2F,3F) O2 | 8 |
| IV | 2CBB(2F,3F)O2 | 12 |
| IV | 3C1OB(2F,3F)O2 | 10 |
| IV | C(5)1OSaO4 | 6 |
| I | I-2-1 | 0.2 |
| Performance of liquid crystal medium | $\Delta\varepsilon$ [1 KHz, 20° C.]: −3.0 $\Delta n$[589 nm, 20° C.]: 0.115 Cp: 97° C.; and $\gamma_1$: 110 mPa · s. | |

TABLE 12

Structure type, code and content of the raw material compound of a liquid crystal medium prepared in Example 19 and the performance of the liquid crystal medium

| Category of compound structural formula | Compound code | Percentage by mass (%) |
|---|---|---|
| II | 3CC2 | 20 |
| II | 3CCV | 18 |
| II | 3CBO2 | 2 |
| III | VCCB1 | 10 |
| IV | 3CCB(2F,3F)O2 | 8 |
| IV | 2CB(2F,3F)B(3F)O2 | 12 |
| IV | 3C1OB(2F,3F)O2 | 10 |
| IV | C(5)BB(2F,3F)O2 | 10 |

TABLE 12-continued

Structure type, code and content of the raw material compound of a liquid crystal medium prepared in Example 19 and the performance of the liquid crystal medium

| Category of compound structural formula | Compound code | Percentage by mass (%) |
|---|---|---|
| IV | 3CB(2F,3F)O2 | 10 |
| I | I-4-1 | 0.2 |
| Performance of liquid crystal medium | $\Delta\varepsilon$ [1 KHz, 20° C.]: −3.5; $\Delta n$[589 nm, 20° C.]: 0.08; Cp: 60° C.; and $\gamma_1$: 90 mPa · s. | |

TABLE 13

Structure type, code and content of the raw material compound of a liquid crystal medium prepared in Example 20 and the performance of the liquid crystal medium

| Category of compound structural formula | Compound code | Percentage by mass (%) |
|---|---|---|
| II | 3CC2 | 30 |
| II | 3CCV | 20 |
| III | VCCB1 | 2 |
| III | V2CCB1 | 3 |
| IV | 1VCCB(2F,3F)O2 | 8 |
| IV | 2CBB(2F,3F)O2 | 12 |
| IV | 3C1OB(2F,3F)O2 | 10 |
| IV | C(5)CB(2F,3F)O2 | 10 |
| IV | 3CB(2F,3F)O2 | 5 |
| I | I-6-1 | 0.3 |
| Performance of liquid crystal medium | $\Delta\varepsilon$ [1 KHz, 20° C.]: −3.0; $\Delta n$[589 nm, 20° C.]: 0.08; Cp: 60° C.; and $\gamma_1$: 82 mPa · s. | |

TABLE 14

Structure type, code and content of the raw material compound of a liquid crystal medium prepared in Example 21 and the performance of the liquid crystal medium

| Category of compound structural formula | Compound code | Percentage by mass (%) |
|---|---|---|
| II | 3CC2 | 16 |
| II | 3CCV | 26 |
| II | 1BB5 | 4 |
| II | 5CB3 | 6 |
| II | 3CC2V1 | 6 |
| II | 3CCV1 | 12 |
| IV | 3CBB(2F,3F)O4 | 8 |
| IV | 3CC1OB(2F,3F)O2 | 6 |
| IV | 3CCB(2F,3F)O4 | 5 |
| IV | 2CBB(2F,3F)O2 | 11 |
| I | I-2-2 | 1 |
| Performance of liquid crystal medium | $\Delta\varepsilon$[1 KHz, 20° C.]: −2.0; $\Delta n$[589 nm, 20° C.]: 0.095; Cp: 72° C.; and $\gamma_1$ 70 mPa · s. | |

TABLE 15

Structure type, code and content of the raw material compound of a liquid crystal medium prepared in Example 22 and the performance of the liquid crystal medium

| Category of compound structural formula | Compound code | Percentage by mass (%) |
|---|---|---|
| II | 3CC2 | 20 |
| III | 3CCB1 | 5 |
| III | V2CCB1 | 10 |
| III | 3CBB2 | 5 |
| III | 3CCB2 | 5 |
| III | VCCB1 | 10 |
| III | 3CBB3 | 5 |
| IV | 2CCB(2F,3F)O2 | 9 |
| IV | 2CBB(2F,3F)O4 | 8 |
| IV | C(5)CBB(2F,3F)O4 | 7 |
| IV | 3CBB(2F,3F)O2 | 10 |
| V | C(5)1OSaO4 | 6 |
| I | I-3-2 | 0.05 |
| Performance of liquid crystal medium | $\Delta\varepsilon$ [1 KHz, 20° C.]: −3.2; $\Delta n$[589 nm, 20° C.]: 0.109; Cp: 72° C.; and $\gamma_1$: 70 mPa · s. | |

TABLE 16

Structure type, code and content of the raw material compound of a liquid crystal medium prepared in Example 23 and the performance of the liquid crystal medium

| Category of compound structural formula | Compound code | Percentage by mass (%) |
|---|---|---|
| II | 3CC2 | 20 |
| II | 3CCV | 18 |
| III | 3CBB(3F)B5 | 5 |
| III | 3CB(3F)BC5 | 5 |
| III | 3C[3O,5O]CB5 | 9 |
| III | 3CC[3O,5O]B5 | 10 |
| IV | 2BB(2F,3F)O2 | 1 |
| VI | 3ODfO4 | 5 |
| VI | 2ODfO5 | 5 |
| VI | 2ODfO4 | 6 |
| V | 3OSaO4 | 5 |
| V | 2OSaO5 | 5 |
| V | C(5)1OSaO4 | 6 |
| I | I-1-2 | 0.5 |
| Performance of liquid crystal medium | $\Delta\varepsilon$ [1 KHz, 20° C.]: −3.5; $\Delta n$[589 nm, 20° C.]: 0.108; Cp: 70° C.; and $\gamma_1$: 75 mPa · s. | |

TABLE 17

Structure type, code and content of the raw material compound of a liquid crystal medium prepared in Example 24 and the performance of the liquid crystal medium

| Category of compound structural formula | Liquid crystal monomer code | Percentage by mass (%) |
|---|---|---|
| II | 3CC2 | 15 |
| II | 3CCV | 35 |
| III | 3CBB2 | 2 |
| III | V2CCB1 | 3 |
| III | 5BBB(2F,4F) | 13 |
| IV | C(3)1CBB(2F,3F)O2 | 17 |
| IV | C(5)CBB (2F,3F)O4 | 6 |
| VI | C(5) 1ODfO4 | 1 |
| V | C(5)1OSaO4 | 3 |
| VI | C(3) 1ODfO4 | 5 |
| I | I-4-2 | 0.2 |
| Performance of liquid crystal medium | $\Delta\varepsilon$ [1 KHz, 20° C.]: −3.6; $\Delta n$[589 nm, 20° C.]: 0.115; Cp: 73° C.; and $\gamma_1$: 76 mPa · s. | |

TABLE 18

Structure type, code and content of the raw material compound of a liquid crystal medium prepared in Example 25 and the performance of the liquid crystal medium

| Category of compound structural formula | Compound code | Percentage by mass (%) |
|---|---|---|
| II | 3CC2 | 5 |
| II | 3CCV | 45 |
| III | 3CBB2 | 5 |
| III | 3CBB3 | 5 |
| III | C(3) 1BB(3F)B5 | 8 |
| IV | C(3) 1CBB(2F,3F)O2 | 5 |
| IV | C(3) 1CBB(2F,3F)O4 | 7 |
| IV | 3CC1OB(2F,3F)O2 | 6 |
| IV | 3CLB(2F,3F)O4 | 6 |
| IV | 3CLB(2F,3F)O2 | 3 |
| IV | 3CB (2F,3F)O2 | 5 |
| I | I-5-2 | 0.35 |
| Performance of liquid crystal medium | $\Delta\varepsilon$ [1 KHz, 20° C.]: −3.5; $\Delta n$[589 nm, 20° C.]: 0.11; Cp: 78° C.; and $\gamma_1$: 72 mPa · s. | |

TABLE 19

Structure type, code and content of the raw material compound of a liquid crystal medium prepared in Example 26 and the performance of the liquid crystal medium

| Category of compound structural formula | Compound code | Percentage by mass (%) |
|---|---|---|
| II | 3CC2 | 1 |
| III | C(3) 1BB(3F)B2 | 5 |
| III | 3CBB3 | 1 |
| III | 5BBB(2F,4F) | 3 |
| IV | 3CB(2F,3F)O2 | 8 |
| IV | 2CB(2F,3F)O2 | 12 |
| IV | 3C1OB(2F,3F)O2 | 10 |
| IV | 3C1OB(2F,3F)O4 | 10 |
| IV | C(5)BB(2F,3F)O2 | 10 |
| IV | 3CBB(2F,3F)O2 | 8 |
| IV | 2CBB(2F,3F)O2 | 12 |
| IV | 3CC1OB(2F,3F)O2 | 10 |
| IV | 3CC1OB(2F,3F)O4 | 10 |
| I | I-1-2 | 0.3 |

TABLE 19-continued

Structure type, code and content of the raw material compound of a liquid crystal medium prepared in Example 26 and the performance of the liquid crystal medium

| Category of compound structural formula | Compound code | Percentage by mass (%) |
|---|---|---|
| Performance of liquid crystal medium | $\Delta\varepsilon$ [1 KHz, 20° C.]: −5.1; $\Delta$n[589 nm, 20° C.]: 0.105; Cp: 75° C.; and $\gamma_1$: 95 mPa · s. | |

It can be seen from Tables 5-19 above that the liquid crystal composition, i.e., liquid crystal medium, provided by the present invention has a very high resistivity a low threshold voltage, and a small response time. In addition, it further has an excellent low-temperature stability, a wide operating temperature range, and also an appropriate rate of polymerization, and when it is used in a liquid crystal display device, in addition to obtaining an excellent display performance, the occurrence of defective panels can also be avoided, improving the product yield.

Obviously, the above-mentioned embodiments of the present invention are merely examples for clearly illustrating the present invention, rather than limiting the embodiments of the present invention; for a person of ordinary skill in the art, on the basis of the above description, other variations or changes in different forms may also be made, all the embodiments cannot be provided exhaustively herein, and any obvious variation or change derived from the technical solution of the present invention is still within the scope of protection of the present invention.

The invention claimed is:

1. A polymerizable compound, characterized in that the structural formula of said polymerizable compound is as represented by the following formula I:

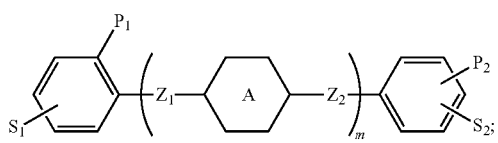

I wherein $P_1$ and $P_2$ each individually represent a substituent containing a polymerizable group, and $P_2$ is singly present;

$S_1$ and $S_2$ are singly present and each independently represent H, a $C_1$-$C_5$ alkyl group, a $C_1$-$C_5$ alkoxy group, a fluorine-substituted $C_1$-$C_5$ alkyl group, a fluorine-substituted $C_1$-$C_5$ alkoxy group, a halogen, an acrylate group, or a methacrylate group, wherein any non-adjacent methylenes may be each independently replaced by —O—, —S—, —CH$_2$O—, —COO—, —OCH$_2$—, —OOC—, an acrylate group or a methacrylate group;

$Z_1$ and $Z_2$ each independently represent a single bond, —CH$_2$—, —CH$_2$CH$_2$—, —O—, —CH$_2$O—, —OCH$_2$—, —COO—, —OOC—, or an acrylate group;

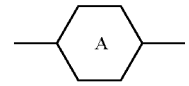

represents 1,4-phenylene, or a 1,4-phenylene mono- or poly-substituted with one or more of H, a $C_1$-$C_5$ alkyl group, a $C_1$-$C_5$ alkoxy group, a fluorine-substituted $C_1$-$C_5$ alkyl group, a fluorine-substituted $C_1$-$C_5$ alkoxy group, a halogen, an acrylate group and a methacrylate group, wherein any non-adjacent methylenes of the $C_1$-$C_5$ alkyl group, $C_1$-$C_5$ alkoxy group, fluorine-substituted $C_1$-$C_5$ alkyl group, and fluorine-substituted $C_1$-$C_5$ alkoxy group may be each independently replaced by —O—, —S—, —CH$_2$O—, —COO—, —OCH$_2$—, —OOC—, an acrylate group or a methacrylate group;

m represents 0, 1 or 2;

when m represents 0;
 (a) neither $S_1$ nor $S_2$ is H, or
 (b) only $S_2$ is not H and $P_2$ is not in the ortho-position of the single bond linking the two benzene rings; and when m represents 1 or 2, $Z_1$ and $Z_2$ are not simultaneously a single bond, or

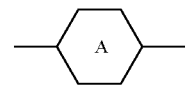

represents a 1,4-phenylene mono- or poly-substituted with one or more of a $C_1$-$C_5$ alkyl group, a $C_1$-$C_5$ alkoxy group, a fluorine-substituted $C_1$-$C_5$ alkyl group, a fluorine-substituted $C_1$-$C_5$ alkoxy group, a halogen, an acrylate group and a methacrylate group, wherein any non-adjacent methylenes of the $C_1$-$C_5$ alkyl group, $C_1$-$C_5$ alkoxy group, fluorine-substituted $C_1$-$C_5$ alkyl group, and fluorine-substituted $C_1$-$C_5$ alkoxy group may be each independently replaced by —O—, —S—, —CH$_2$O—, —COO—, —OCH$_2$—, —OOC—, an acrylate group or a methacrylate group.

2. The polymerizable compound according to claim 1, characterized in that the structural formula of said polymerizable compound of structural formula I is specifically as represented by the following formula I-a:

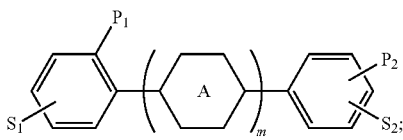

I-a wherein $P_1$ and $P_2$ each independently represent a substituent containing an acrylate group, a methacrylate group, a fluorine-substituted acrylate group or a fluorine-substituted methacrylate group;

$S_1$ and $S_2$ are singly present and each independently represent H, F, a $C_1$-$C_5$ alkyl group, a $C_1$-$C_5$ alkoxy group, a fluorine-substituted $C_1$-$C_5$ alkyl group, a fluorine-substituted $C_1$-$C_5$ alkoxy group, an acrylate group, a methacrylate group;

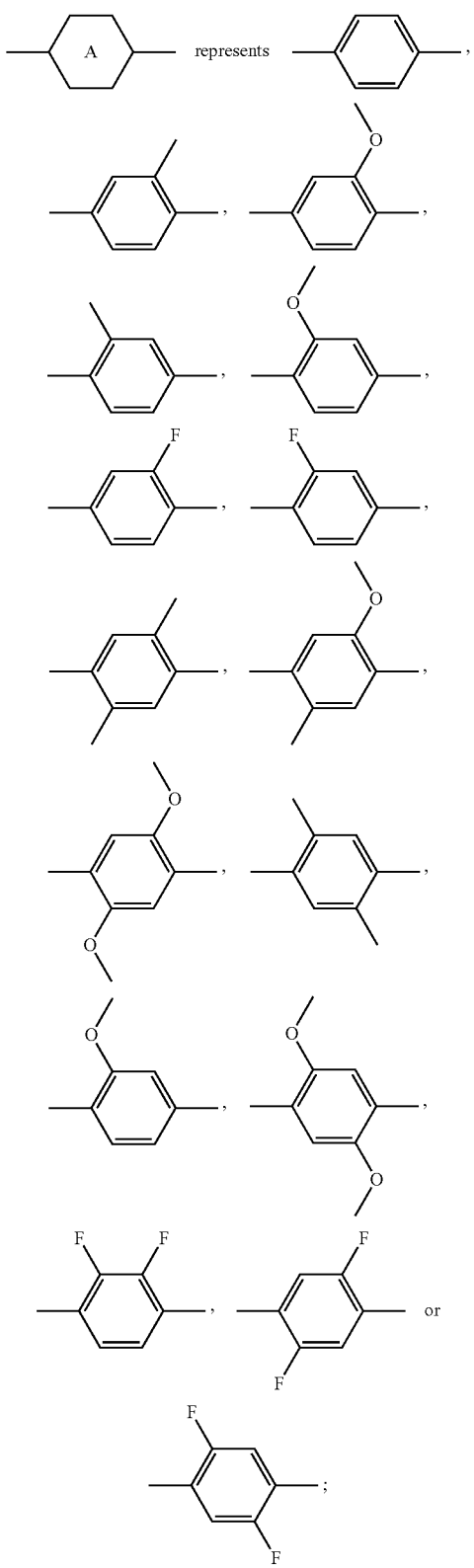

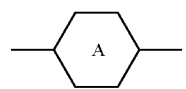 represents m represents 0 or 1; and when m represents 0, (a) neither $S_1$ nor $S_2$ is H, or (b) only $S_2$ is not H and $P_2$ is not in the ortho-position of the single bond linking the two benzene rings; and when m represents 1,

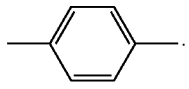

is not

3. The polymerizable compound according to claim 1, characterized in that the structural formula of said polymerizable compound of structural formula I is specifically at least one of formulas I-1 to I-6 below:

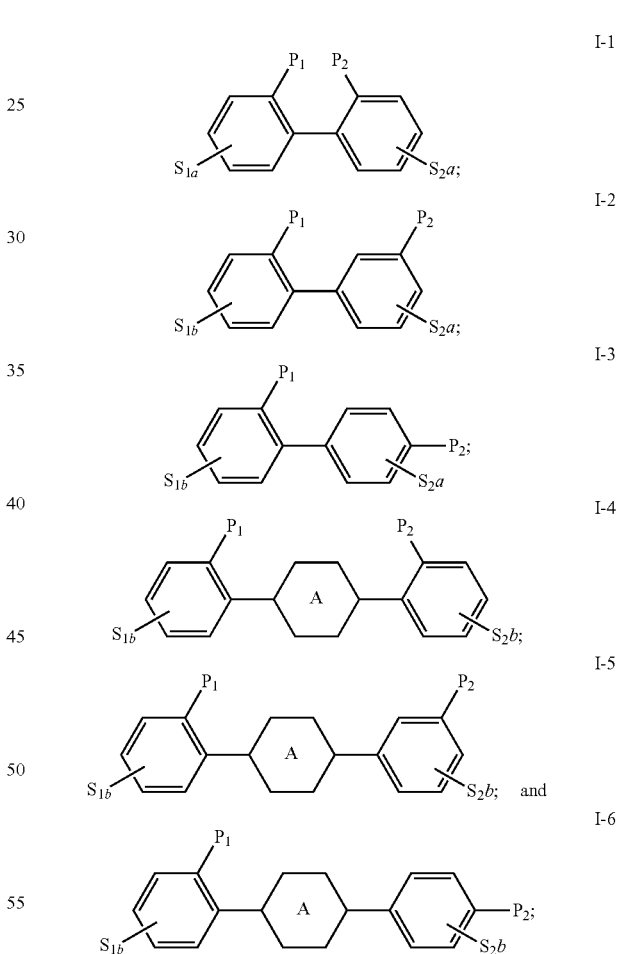

wherein $P_1$ and $P_2$ each independently represent an acrylate group or a methacrylate group;

$S_{1a}$ represents F, methyl or methoxy;

$S_{1b}$ represents H, F, methyl or methoxy;

$S_2a$ represents F, methyl or methoxy;

$S_2b$ represents H, F, methyl or methoxy;

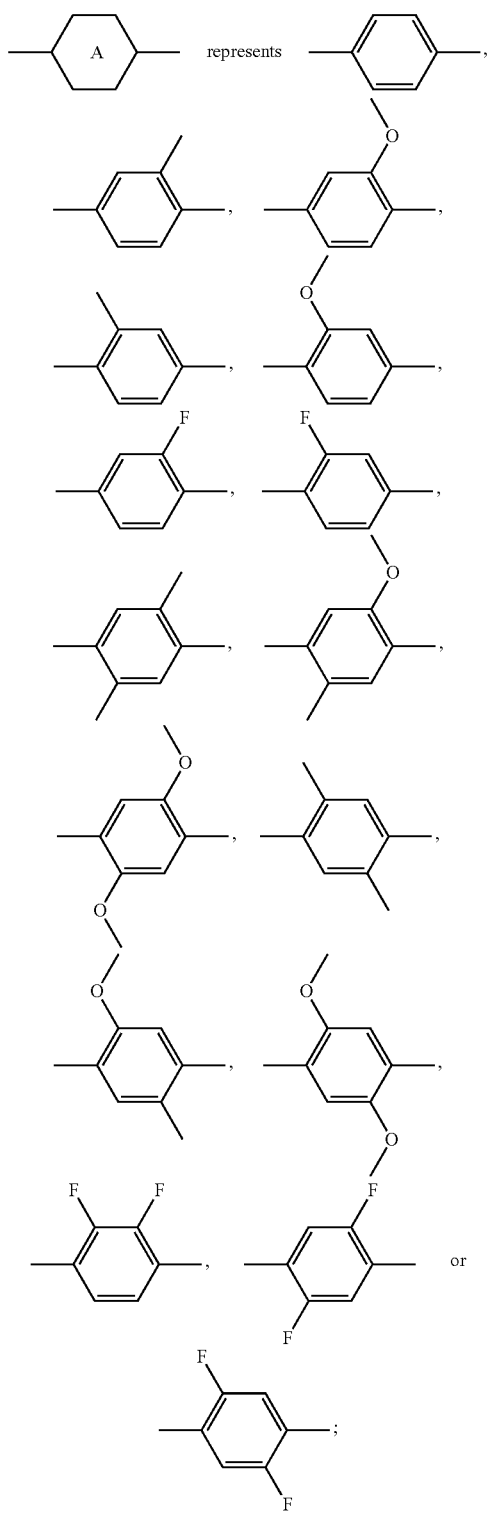
and when S₂b represents H,
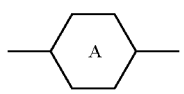
is not
4. A liquid crystal medium, characterized by comprising one or more polymerizable compounds of claim 1.
5. The liquid crystal medium according to claim 4, characterized in that said liquid crystal medium further comprises one or more compounds of structural formulas II-1 to II-12 and/or of formula III:
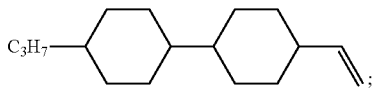  II-1
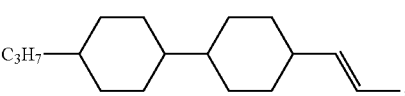  II-2
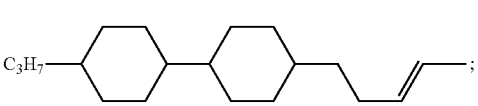  II-3
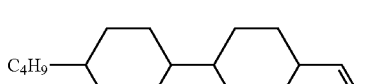  II-4
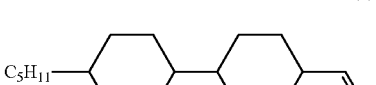  II-5
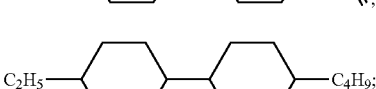  II-6
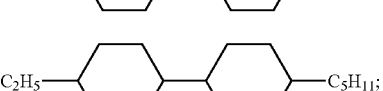  II-7
  II-8
  II-9
  II-10
  II-11
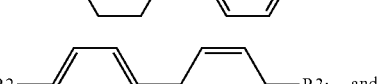  II-12
and

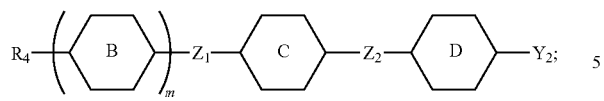

wherein
$R_0$, $R_1$, $R_2$ and $R_3$ each independently represent a $C_1$-$C_{10}$ alkyl group, a $C_2$-$C_{10}$ alkenyl group, or a $C_1$-$C_{10}$ alkoxy group, wherein any —$CH_2$— can be replaced by —O—, and any hydrogen can be replaced by F;

$R_4$ and $Y_2$ each independently represent H, F, a $C_1$-$C_{10}$ alkyl group, a fluorine-substituted $C_1$-$C_{10}$ alkyl group, a $C_1$-$C_{10}$ alkoxy group, a fluorine-substituted $C_1$-$C_{10}$ alkoxy group, a $C_2$-$C_{10}$ alkenyl group, a fluorine-substituted $C_2$-$C_{10}$ alkenyl group, a $C_3$-$C_8$ alkenyloxy group or a fluorine-substituted $C_3$-$C_8$ alkenyloxy group, wherein any one or more —$CH_2$— in $R_4$ may be replaced by cyclopentyl, cyclobutyl or cyclopropyl;

$Z_1$ and $Z_2$ each independently represent a single bond, —$CF_2O$—, —$CH_2CH_2$— or —$CH_2O$—,

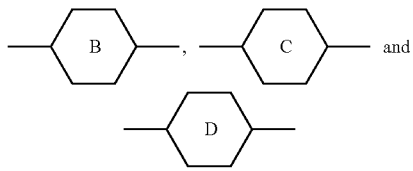

each independently represent

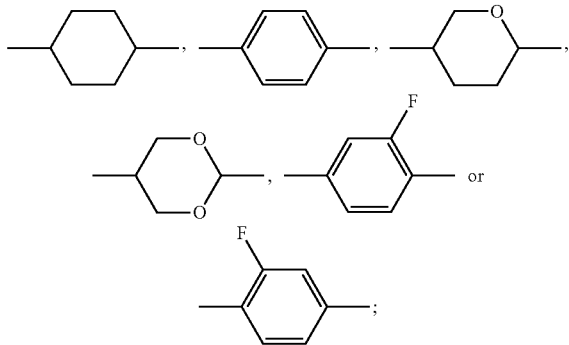

m represents 1 or 2.

6. The liquid crystal medium according to claim 4, characterized in that said liquid crystal medium further comprises one or more compounds of structural formula IV

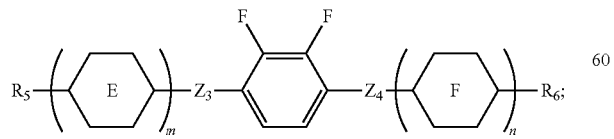

wherein
$R_5$ and $R_6$ each independently represent H, F, a $C_1$-$C_{10}$ alkyl group, a fluorine-substituted $C_1$-$C_{10}$ alkyl group, a $C_1$-$C_{10}$ alkoxy group, a fluorine-substituted $C_1$-$C_{10}$ alkoxy group, a $C_2$-$C_{10}$ alkenyl group, a fluorine-substituted $C_2$-$C_{10}$ alkenyl group, a $C_3$-$C_8$ alkenyloxy group or a fluorine-substituted $C_3$-$C_8$ alkenyloxy group, wherein any one of —$CH_2$— in $R_5$ and $R_6$ may be replaced by cyclopentyl, cyclobutyl or cyclopropyl;

$Z_3$ and $Z_4$ each independently represent a single bond, —$CH_2CH_2$— or —$CH2O$—;

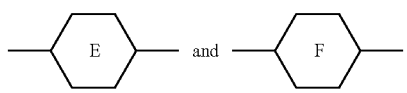

each independently represent one of

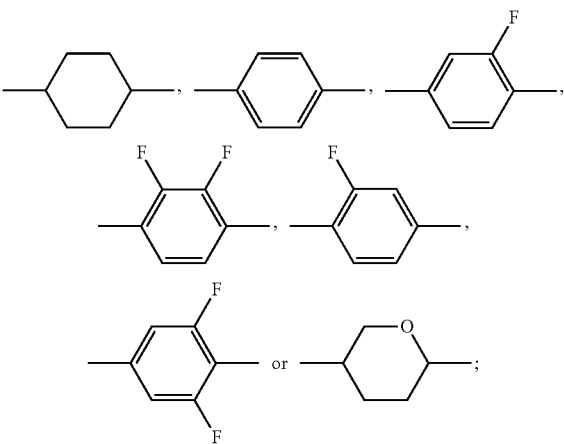

m represents 1 or 2; and
n represents 0, 1 or 2.

7. The liquid crystal medium according to claim 4, characterized in that the structural formula of said compound of structural formula III is specifically at least one of formulas III-1 to III-9 below:

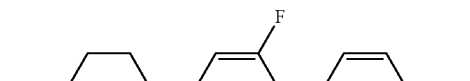

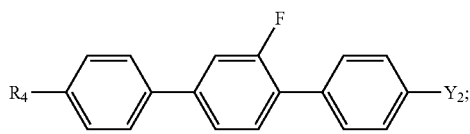

-continued

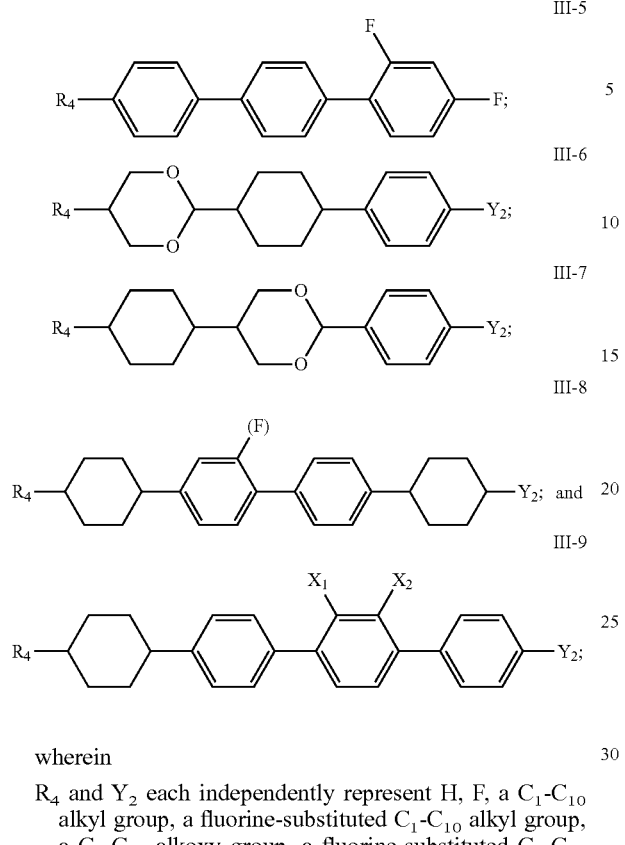

wherein

R$_4$ and Y$_2$ each independently represent H, F, a C$_1$-C$_{10}$ alkyl group, a fluorine-substituted C$_1$-C$_{10}$ alkyl group, a C$_1$-C$_{10}$ alkoxy group, a fluorine-substituted C$_1$-C$_{10}$ alkoxy group, a C$_2$-C$_{10}$ alkenyl group, a fluorine-substituted C$_2$-C$_{10}$ alkenyl group, a C$_3$-C$_8$ alkenyloxy group or a fluorine-substituted C$_3$-C$_8$ alkenyloxy group, wherein any —CH$_2$— in R$_4$ may be replaced by cyclopentyl, cyclobutyl or cyclopropyl;

(F) represents H or F; and

X$_1$ and X$_2$ each independently represent H or F, but X$_1$ and X$_2$ are neither H at the same time nor F at the same time.

8. The liquid crystal medium according to claim 6, characterized in that the structural formula of said compound of structural formula IV is specifically at least one of formulas IV-1 to IV-13 below:

wherein

R$_5$ and R$_6$ each independently represent H, a C$_1$-C$_{10}$ alkyl group, a fluorine-substituted C$_1$-C$_{10}$ alkyl group, a C$_1$-C$_{10}$ alkoxy group, a fluorine-substituted C$_1$-C$_{10}$ alkoxy group, a C$_2$-C$_{10}$ alkenyl group, a fluorine-substituted C$_2$-C$_{10}$ alkenyl group, a C$_3$-C$_8$ alkenyloxy group or a fluorine-substituted C$_3$-C$_8$ alkenyloxy group, wherein any one of —CH$_2$— in R$_5$ and R$_6$ may be replaced by cyclopentyl, cyclobutyl or cyclopropyl.

9. The liquid crystal medium according to claim 6, characterized in that said liquid crystal medium further comprises one or more compounds of structural formula V and/or structural formula VI:

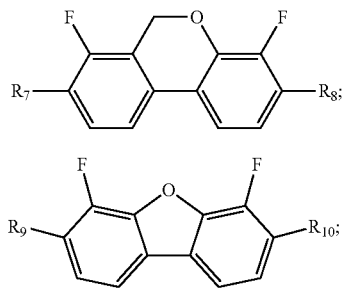

wherein

R$_7$, R$_8$, R$_9$ and R$_{10}$ each independently represent H, F, a C$_1$-C$_{10}$ alkyl group, a fluorine-substituted C$_1$-C$_{10}$ alkyl group, a C$_1$-C$_{10}$ alkoxy group, a fluorine-substituted C$_1$-C$_{10}$ alkoxy group, a C$_2$-C$_{10}$ alkenyl group, a fluorine-substituted C$_2$-C$_{10}$ alkenyl group, a C$_3$-C$_8$ alkenyloxy group or a fluorine-substituted C$_3$-C$_8$ alkenyloxy group.

10. The liquid crystal medium according to claim 5, characterized in that in said liquid crystal medium, the content in percentage by weight of the polymerizable compound of structural formula I is 0.001-5%, and the content in percentage by weight of the one or more compounds of structural formulas II-1 to II-12 or the one or more compounds of structural formula III is 0-70%.

11. The liquid crystal medium according to claim 10, characterized in that in said liquid crystal medium, the content in percentage by mass of the polymerizable compound of structural formula I is 0.05-2%, the content in percentage by mass of the one or more compounds of structural formulas II-1 to II-10 is 1-60%, and the content in percentage by mass of the one or more compounds of structural formula formulas II-11 and II-12 is 0-30%; wherein in formula II-11, R0 and R1 each independently represent a C$_1$-C$_5$ alkyl group or a C$_2$-C$_5$ alkenyl group; and in formula II-12, R$_2$ and R$_3$ each independently represent a C$_1$-C$_5$ alkyl group or a C$_1$-C$_5$ alkoxy group.

12. The liquid crystal medium, characterized in that in said liquid crystal medium, a content in percentage by mass of the polymerizable compound of structural formula I is 0.1-1%, a content in percentage by mass of the compound of structural formula III is 0-40%, a content in percentage by mass of the compound of structural formula IV is 1-90%, a content in percentage by mass of the compound of structural formula V is 0-20%, and a content in percentage by mass of the compound of structural formula VI is 0-30%:

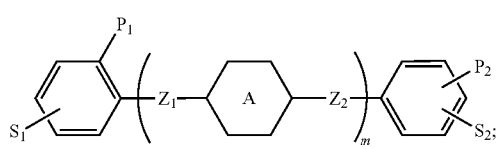

wherein in formula I:

P$_1$ and P$_2$ each individually represent a polymerizable group, and P$_2$ is singly present;

S$_1$ and S$_2$ are singly present and each independently represent H, a C$_1$-C$_5$ alkyl group, a C$_1$-C$_5$ alkoxy group, a fluorine-substituted C$_1$-C$_5$ alkyl group, a fluorine-substituted C$_1$-C$_5$ alkoxy group, a halogen, an acrylate group, or a methacrylate group, wherein any non-adjacent methylenes may be each independently replaced by —O—, —S—, —CH$_2$O—, —COO—, —OCH$_2$—, —OOC—, an acrylate group or a methacrylate group;

Z$_1$ and Z$_2$ each independently represent a single bond, —CH$_2$—, —CH$_2$CH$_2$—, —O—, —CH$_2$O—, —OCH$_2$—, —COO—, —OOC—, or an acrylate group;

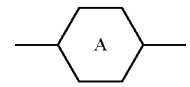

represents 1,4-phenylene, or a 1,4-phenylene mono— or poly-substituted with one or more of H, a C$_1$-C$_5$ alkyl group, a C$_1$-C$_5$ alkoxy group, a fluorine-substituted C$_1$-C$_5$ alkyl group, a fluorine-substituted C$_1$-C$_5$ alkoxy group, a halogen, an acrylate group and a methacrylate group, wherein any non-adjacent methylenes of the C$_1$-C$_5$ alkyl group, C$_1$-C$_5$ alkoxy group, fluorine-substituted C$_1$-C$_5$ alkyl group, and fluorine-substituted C$_1$-C$_5$ alkoxy group may be each independently replaced by —O—, —S—, —CH$_2$O—, —COO—, —OCH$_2$—, —OOC—, an acrylate group or a methacrylate group;

m represents 0, 1 or 2;

when m represents 0:
(a) neither S$_1$ nor S$_2$ is H, or
(b) only S$_2$ is not H and P$_2$ is not in the ortho-position of the single bond linking the two benzene rings; and when m represents 1 or 2, Z$_1$ and Z$_2$ are not simultaneously a single bond, or

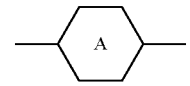

represents a 1,4—phenylene mono— or poly-substituted with one or more of a C$_1$-C$_5$ alkyl group, a C$_1$-C$_5$ alkoxy group, a fluorine-substituted C$_1$-C$_5$ alkyl group, a fluorine-substituted C$_1$-C$_5$ alkoxy group, a halogen, an acrylate group and a methacrylate group, wherein any non-adjacent methylenes of the C$_1$-C$_5$ alkyl group, C$_1$-C$_5$ alkoxy group, fluorine-substituted C$_1$-C$_5$ alkyl group, and fluorine-substituted C$_1$-C$_5$ alkoxy group may be each independently replaced by —O—, —S—, —CH$_2$O—, —COO—, —OCH$_2$—, —OOC—, an acrylate group or a methacrylate group;

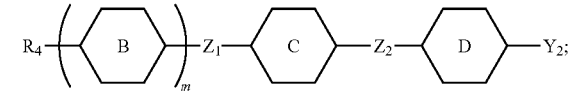

wherein in formula III:

R$_0$, R$_1$, R$_2$ and R$_3$ each independently represent a C$_1$-C$_{10}$ alkyl group, a C$_2$-C$_{10}$ alkenyl group, or a C$_1$-C$_{10}$ alkoxy group, wherein any —CH$_2$— can be replaced by —O—, and any hydrogen can be replaced by F;

R$_4$ and Y$_2$ each independently represent H, F, a C$_1$-C$_{10}$ alkyl group, a fluorine-substituted C$_1$-C$_{10}$ alkyl group, a C$_1$-C$_{10}$ alkoxy group, a fluorine-substituted C$_1$-C$_{10}$ alkoxy group, a C$_2$-C$_{10}$ alkenyl group, a fluorine-substituted C$_2$-C$_{10}$ alkenyl group, a C$_3$-C$_8$ alkenyloxy group or a fluorine-substituted C$_3$-C$_8$ alkenyloxy group, wherein any one or more —CH$_2$— in R$_4$ may be replaced by cyclopentyl, cyclobutyl or cyclopropyl;

Z$_1$ and Z$_2$ each independently represent a single bond, —CF$_2$O—, —CH$_2$CH$_2$— or —CH$_2$O—;

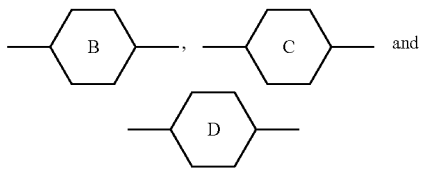

each independently represent

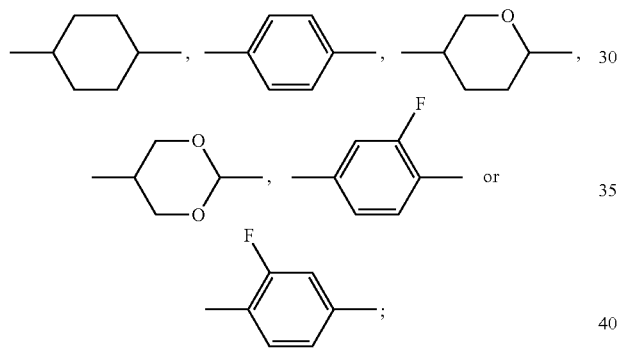

and m represents 1 or 2;

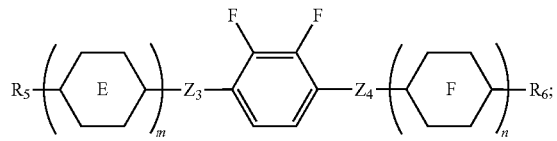

IV wherein in formula IV:

R$_5$ and R$_6$ each independently represent H, F, a C$_1$-C$_{10}$ alkyl group, a fluorine-substituted C$_1$-C$_{10}$ alkyl group, a C$_1$-C$_{10}$ alkoxy group, a fluorine-substituted C$_1$-C$_{10}$ alkoxy group, a C$_2$-C$_{10}$ alkenyl group, a fluorine-substituted C$_2$-C$_{10}$ alkenyl group, a C$_3$-C$_8$ alkenyloxy group or a fluorine-substituted C$_3$-C$_8$ alkenyloxy group, wherein any one of —CH$_2$— in R$_5$ and R$_6$ may be replaced by cyclopentyl, cyclobutyl or cyclopropyl;

Z$_3$ and Z$_4$ each independently represent a single bond, —CH$_2$CH$_2$— or —CH$_2$O—;

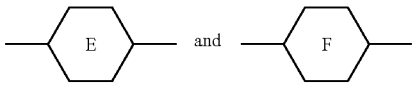

each independently represent one of

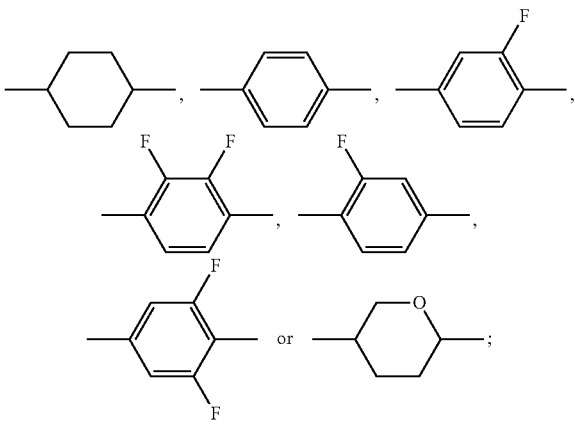

m represents 1 or 2; and
n represents 0, 1 or 2;

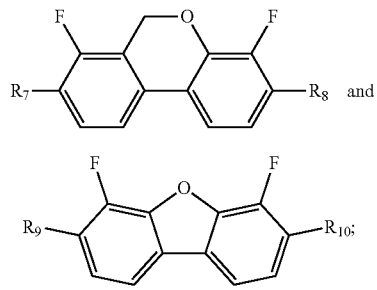

wherein in formulas V and VI:

R$_7$, R$_8$, R$_9$ and R$_{10}$ each independently represent H, F, a C$_1$-C$_{10}$ alkyl group, a fluorine-substituted C$_1$-C$_{10}$ alkyl group, a C$_1$-C$_{10}$ alkoxy group, a fluorine-substituted C$_1$-C$_{10}$ alkoxy group, a C$_2$-C$_{10}$ alkenyl group, a fluorine-substituted C$_2$-C$_{10}$ alkenyl group, a C$_3$-C$_8$ alkenyloxy group or a fluorine-substituted C$_3$-C$_8$ alkenyloxy group, wherein any one of —CH$_2$— in R$_5$ and R$_6$ may be replaced by cyclopentyl, cyclobutyl or cyclopropyl.

13. A liquid crystal display device, characterized in that said liquid crystal display device is prepared from the liquid crystal medium of claim 4.

* * * * *